(12) United States Patent
Schramm et al.

(10) Patent No.: US 9,845,523 B2
(45) Date of Patent: Dec. 19, 2017

(54) METHODS FOR SHAPING HIGH ASPECT RATIO ARTICLES FROM METALLIC GLASS ALLOYS USING RAPID CAPACITIVE DISCHARGE AND METALLIC GLASS FEEDSTOCK FOR USE IN SUCH METHODS

(71) Applicant: Glassimetal Technology, Inc., Pasadena, CA (US)

(72) Inventors: Joseph P. Schramm, Sierra Madre, CA (US); Jong Hyun Na, Pasadena, CA (US); Marios D. Demetriou, West Hollywood, CA (US); David S. Lee, Wenham, MA (US); William L. Johnson, San Marino, CA (US)

(73) Assignees: Glassimetal Technology, Inc., Pasadena, CA (US); Apple Inc., Cupertino, CA (US)

( * ) Notice: Subject to any disclaimer, the term of this patent is extended or adjusted under 35 U.S.C. 154(b) by 587 days.

(21) Appl. No.: 14/216,565

(22) Filed: Mar. 17, 2014

(65) Prior Publication Data
US 2014/0283956 A1 Sep. 25, 2014
US 2015/0197837 A9 Jul. 16, 2015

Related U.S. Application Data

(60) Provisional application No. 61/793,904, filed on Mar. 15, 2013.

(51) Int. Cl.
*C21D 1/54* (2006.01)
*C22C 45/00* (2006.01)
(Continued)

(52) U.S. Cl.
CPC .............. *C22C 45/00* (2013.01); *A61L 27/04* (2013.01); *C21D 1/40* (2013.01); *C22B 4/06* (2013.01);
(Continued)

(58) Field of Classification Search
CPC ........ C21D 1/40; C21D 2201/03; C22B 4/06; C22C 1/002; C22C 45/00; C22F 1/002
See application file for complete search history.

(56) References Cited

U.S. PATENT DOCUMENTS 2,816,034 A 12/1957 Mittelmann
3,332,747 A 7/1967 Bundy
(Continued)

FOREIGN PATENT DOCUMENTS

CN 1552940 12/2004
CN 1689733 11/2005
(Continued)

OTHER PUBLICATIONS

Saotome et al., "Characteristic behavior of Pt-based metallic glass under rapid heating and its application to microforming," *Materials Science and Engineering A*, 2004, vol. 375-377, pp. 389-393.
(Continued)

*Primary Examiner* — Colleen Dunn
*Assistant Examiner* — Nicholas Wang
(74) *Attorney, Agent, or Firm* — Polsinelli PC

(57) ABSTRACT

The disclosure is directed to a method of forming high-aspect-ratio metallic glass articles that are substantially free of defects and cosmetic flaws by means of rapid capacitive discharge forming. Metallic glass alloys that are stable against crystallization for at least 100 ms at temperatures where the viscosity is in the range of $10^0$ to $10^4$ Pa-s are considered as suitable for forming such high-aspect-ratio articles.

15 Claims, 10 Drawing Sheets

(51) Int. Cl.

| | | |
|---|---|---|
| *C21D 1/40* | (2006.01) | |
| *C22F 1/00* | (2006.01) | |
| *C22F 1/10* | (2006.01) | |
| *C22B 4/06* | (2006.01) | |
| *C22C 1/00* | (2006.01) | |
| *C22C 45/04* | (2006.01) | |
| *A61L 27/04* | (2006.01) | |

(52) U.S. Cl.
CPC ............ *C22C 1/002* (2013.01); *C22C 45/001* (2013.01); *C22C 45/04* (2013.01); *C22F 1/002* (2013.01); *C22F 1/10* (2013.01); *C21D 2201/03* (2013.01)

(56) References Cited

U.S. PATENT DOCUMENTS

| | | | |
|---|---|---|---|
| 3,537,045 A | 10/1970 | Ichiro | |
| 3,863,700 A | 2/1975 | Bedell et al. | |
| 4,115,682 A | 9/1978 | Kavesh et al. | |
| 4,355,221 A | 10/1982 | Lin | |
| 4,715,906 A | 12/1987 | Taub et al. | |
| 4,809,411 A | 3/1989 | Lin et al. | |
| 4,950,337 A | 8/1990 | Li et al. | |
| 5,005,456 A | 4/1991 | Ballard et al. | |
| 5,069,428 A | 12/1991 | Li et al. | |
| 5,075,051 A | 12/1991 | Ito et al. | |
| 5,278,377 A | 1/1994 | Tsai | |
| 5,288,344 A | 2/1994 | Peker et al. | |
| 5,324,368 A | 6/1994 | Masumoto et al. | |
| 5,368,659 A | 11/1994 | Peker et al. | |
| 5,550,857 A | 8/1996 | Richards | |
| 5,554,838 A | 9/1996 | Berdich | |
| 5,618,359 A | 4/1997 | Lin et al. | |
| 5,735,975 A | 4/1998 | Lin et al. | |
| 5,896,642 A | 4/1999 | Peker et al. | |
| 6,027,586 A | 2/2000 | Masumoto et al. | |
| 6,235,381 B1 | 5/2001 | Sanders et al. | |
| 6,258,183 B1 | 7/2001 | Onuki et al. | |
| 6,279,346 B1 | 8/2001 | Ribes et al. | |
| 6,293,155 B1 | 9/2001 | Babiel | |
| 6,355,361 B1 | 3/2002 | Ueno et al. | |
| 6,432,350 B1 | 8/2002 | Seres et al. | |
| 6,771,490 B2 | 8/2004 | Peker et al. | |
| 6,875,293 B2 | 4/2005 | Peker | |
| 7,120,185 B1 | 10/2006 | Richards | |
| 7,506,566 B2 | 3/2009 | Decristofaro et al. | |
| 7,883,592 B2 | 2/2011 | Hofmann et al. | |
| 8,099,982 B2 | 1/2012 | Takagi et al. | |
| 8,276,426 B2 | 10/2012 | Musat et al. | |
| 8,499,598 B2 | 8/2013 | Johnson et al. | |
| 8,613,813 B2 | 12/2013 | Johnson et al. | |
| 8,613,814 B2 | 12/2013 | Kaltenboeck et al. | |
| 8,613,815 B2 | 12/2013 | Johnson et al. | |
| 8,613,816 B2 | 12/2013 | Kaltenboeck et al. | |
| 2001/0033304 A1 | 10/2001 | Ishinaga et al. | |
| 2003/0056562 A1 | 3/2003 | Kamano | |
| 2003/0183310 A1 | 10/2003 | McRae | |
| 2003/0222122 A1* | 12/2003 | Johnson ............... | B22D 11/001 228/101 |
| 2004/0035502 A1 | 2/2004 | Kang et al. | |
| 2005/0034787 A1 | 2/2005 | Song et al. | |
| 2005/0103271 A1 | 5/2005 | Watanabe et al. | |
| 2005/0202656 A1 | 9/2005 | Ito et al. | |
| 2005/0236071 A1 | 10/2005 | Koshiba et al. | |
| 2006/0102315 A1 | 5/2006 | Lee et al. | |
| 2006/0293162 A1 | 12/2006 | Ellison | |
| 2007/0003782 A1 | 1/2007 | Collier | |
| 2007/0034304 A1 | 2/2007 | Inoue et al. | |
| 2008/0081213 A1 | 4/2008 | Ito et al. | |
| 2008/0135138 A1 | 6/2008 | Duan et al. | |
| 2008/0302775 A1 | 12/2008 | Machrowicz | |
| 2009/0236017 A1* | 9/2009 | Johnson ................. | C21D 1/34 148/561 |
| 2010/0009212 A1 | 1/2010 | Utsunomiya et al. | |
| 2010/0047376 A1 | 2/2010 | Imbeau et al. | |
| 2010/0121471 A1 | 5/2010 | Higo et al. | |
| 2010/0320195 A1 | 12/2010 | Fujita et al. | |
| 2011/0048587 A1* | 3/2011 | Vecchio ................... | C21D 1/26 148/561 |
| 2012/0103478 A1 | 5/2012 | Johnson et al. | |
| 2012/0132625 A1* | 5/2012 | Kaltenboeck ............ | C21D 1/34 219/121.11 |
| 2013/0025814 A1* | 1/2013 | Demetriou ............... | C21D 1/40 164/250.1 |
| 2013/0048152 A1* | 2/2013 | Na .......................... | C22C 1/002 148/403 |
| 2013/0319062 A1 | 12/2013 | Johnson et al. | |
| 2014/0033787 A1 | 2/2014 | Johnson et al. | |
| 2014/0047888 A1 | 2/2014 | Johnson et al. | |
| 2014/0083150 A1 | 3/2014 | Kaltenboeck et al. | |
| 2014/0102163 A1 | 4/2014 | Kaltenboeck et al. | |
| 2015/0096967 A1 | 4/2015 | Lee et al. | |
| 2015/0231675 A1 | 8/2015 | Johnson et al. | |
| 2015/0367410 A1 | 12/2015 | Schramm et al. | |
| 2016/0298205 A1 | 10/2016 | Johnson et al. | |

FOREIGN PATENT DOCUMENTS

| | | |
|---|---|---|
| CN | 201838352 | 5/2011 |
| CN | 103320783 | 9/2013 |
| FR | 2806019 | 9/2001 |
| GB | 215522 | 5/1924 |
| GB | 2148751 | 6/1985 |
| JP | 48-008694 | 3/1973 |
| JP | 63-220950 | 9/1988 |
| JP | H06-57309 | 3/1994 |
| JP | H06-277820 | 10/1994 |
| JP | H 08-024969 | 1/1996 |
| JP | 08-300126 | 11/1996 |
| JP | 10-263739 | 10/1998 |
| JP | 10-296424 | 11/1998 |
| JP | 11-001729 | 1/1999 |
| JP | 11-104810 | 4/1999 |
| JP | 11-123520 | 11/1999 |
| JP | 11-354319 | 12/1999 |
| JP | 2000-119826 | 4/2000 |
| JP | 2000-169947 | 6/2000 |
| JP | 2001-321847 | 11/2001 |
| JP | 2001-347355 | 12/2001 |
| JP | 2003-509221 | 3/2003 |
| JP | 2005-209592 | 8/2005 |
| JP | 2008-000783 | 1/2008 |
| JP | 2011-517623 | 6/2011 |
| JP | 2013-530045 | 7/2013 |
| KR | 10-0271356 | 11/2000 |
| WO | WO 01/21343 | 3/2001 |
| WO | WO 2009/117735 | 9/2009 |
| WO | WO 2011/127414 | 10/2011 |
| WO | WO 2012/051443 | 4/2012 |
| WO | WO 2012/092208 | 7/2012 |
| WO | WO 2012/103552 | 8/2012 |
| WO | WO 2012/112656 | 8/2012 |
| WO | WO 2014/078697 | 5/2014 |

OTHER PUBLICATIONS

Kulik et al., "Effect of flash- and furnace annealing on the magnetic and mechanical properties of metallic glasses," *Materials Science and Engineering*, A133 (1991), pp. 232-235.

Masuhr et al., Time Scales for Viscous Flow, Atomic Transport, and Crystallization in the Liquid and Supercooled Liquid States of Zr41.2Ti13.8Cu12.5Ni10.0Be22.5,: *Phys. Rev. Lett.*, vol. 82, (1999), pp. 2290-2293.

Schroers et al., "Pronounced asymmetry in the crystallization behavior during constant heating and cooling of a bulk metallic glass-forming liquid," *Phys. Rev. B*, vol. 60, No. 17 (1999), pp. 11855-11858.

U.S. Appl. No. 14/081,858, filed Nov. 15, 2013, Lee et al.

De Oliveira et al., "Electromechanical engraving and writing on bulk metallic glasses", Applied Physics Letters, Aug. 26, 2002, vol. 81, No. 9, pp. 1606-1608.

(56) References Cited

OTHER PUBLICATIONS

Duan et al., "Bulk Metallic Glass with Benchmark Thermoplastic Processability", Adv. Mater., 2007, vol. 19, pp. 4272-4275.

Ehrt et al., "Electrical conductivity and viscosity of borosilicate glasses and melts," Phys. Chem. Glasses: Eur. J. Glass Sci. Technol. B, Jun. 2009, 50(3), pp. 165-171.

Love, "Temperature dependence of electrical conductivity and the probability density function," J. Phys. C: Solid State Phys., 16, 1983, pp. 5985-5993.

Mattern et al., "Structural behavior and glass transition of bulk metallic glasses, "Journal of Non-Crystalline Solids, 345&346, 2004, pp. 758-761.

Wiest et al., "Zi—Ti-based Be-bearing glasses optimized for high thermal stability and thermoplastic formability", Acta Materialia, 2008, vol. 56, pp. 2625-2630.

Yavari et al., "Electromechanical shaping, assembly and engraving of bulk metallic glasses", Materials Science and Engineering A, 2004, vol. 375-377, pp. 227-234.

Yavari et al., "Shaping of Bulk Metallic Glasses by Simultaneous Application of Electrical Current and Low Stress", Mat. Res. Soc. Symp. Proc., 2001, vol. 644, pp. L12.20.1-L12.20.6.

Demetriou, Document cited and published during Applicant Interview Summary conducted on Jan. 29, 2013, entitled, "Rapid Discharge Heating & Forming of Metallic Glasses: Concepts, Principles, and Capabilities," Marios Demetriou, 20 pages.

U.S. Appl. No. 14/501,563, filed Sep. 30, 2014, Lee et al.

\* cited by examiner

METHODS FOR SHAPING HIGH ASPECT RATIO ARTICLES FROM METALLIC GLASS ALLOYS USING RAPID CAPACITIVE DISCHARGE AND METALLIC GLASS FEEDSTOCK FOR USE IN SUCH METHODS

CROSS-REFERENCE TO RELATED APPLICATIONS

The present application claims the benefit of U.S. Provisional Patent Application No. 61/793,904, entitled "Methods for Shaping High Aspect Ratio Articles from Metallic Glass Alloys Using Rapid Capacitive Discharge and Metallic Glass Feedstock for Use in Such Methods", filed on Mar. 15, 2013, which is incorporated herein by reference in its entirety.

FIELD

The present disclosure is directed to methods and metallic glass alloy feedstock that are capable of being shaped into high aspect ratio articles using rapid capacitive discharge forming.

BACKGROUND

U.S. Patent Publication No. 2009/0236017 is directed to a method of rapidly heating and shaping a metallic glass using a rapid discharge of electrical current. A quantum of electrical energy is discharged with near uniformity through a metallic glass feedstock having a substantially uniform cross-section. The sample is rapidly heated substantially uniformly to a processing temperature between the glass transition temperature of the amorphous phase and the equilibrium melting temperature of the alloy. Either simultaneously or subsequently, the sample is shaped and cooled to form an amorphous article. U.S. Patent Publication No. 2012/0103478 is directed to a metallic glass article having a high aspect ratio that is fabricated by this rapid capacitive discharge forming (RCDF) method.

Both U.S. Patent Publication No. 2009/0236017 and U.S. Patent Publication No. 20120103478 are incorporated herein by reference in their entirety. While both publications disclose a wide-range of materials that may be used with the described methods, neither publication discloses specific ranges of properties of metallic glass alloys for the RCDF method such that the alloys are capable of being shaped into high aspect ratio metallic glass articles.

BRIEF SUMMARY

In one aspect, the disclosure is directed to a method of shaping high-aspect ratio articles. A feedstock is formed of a metallic glass alloy that has a uniform cross-section capable of resisting crystallization for at least 100 ms at a temperature above the glass transition of the alloy where the viscosity of the metallic glass is between $10^0$-$10^4$ Pa-s. In some variations, the viscosity of the metallic glass is between $10^1$-$10^3$ Pa-s. In other variations, the viscosity of the metallic glass is between $10^2$-$10^4$ Pa-s. In some embodiments, the feedstock is capable of resisting crystallization for at least 100 ms at a temperature above the glass transition of the alloy where the viscosity of the metallic glass is between $10^0$-$10^4$ Pa-s. Likewise, in some embodiments the viscosity of the metallic glass is between $10^1$-$10^3$ Pa-s, while in other embodiments the viscosity of the metallic glass is between $10^2$-$10^4$ Pa-s. A quantum of electrical energy is applied to the feedstock, thereby heating the feedstock to a processing window at a temperature within the viscosity range. At such temperature, the heated feedstock is shaped into a high-aspect-ratio article. The shaped article is cooled to a temperature below the glass transition temperature of the metallic glass sufficiently fast to avoid crystallization of the metallic glass. In some variations, the shaped amorphous article has a high aspect ratio of at least 10.

In other variations, the shaped amorphous article has thickness of 2 mm or less. In some further embodiments, the thickness is in the range of 0.5 to 2 mm.

In additional aspects, the present disclosure is directed to methods of screening metallic glass forming alloys for use in making a high aspect ratio metallic glass article. A quantum of electric energy is applied to a sample of metallic glass alloy to heat the sample to a temperature above the glass transition temperature of the alloy, where the viscosity of the metallic glass is between $10^0$ and $10^4$ Pa-s, or alternatively between $10^2$ and $10^4$ Pa-s, or alternatively between $10^2$ and $10^4$ Pa-s. The temperature of the sample is measured. Once the quantum of electric energy has been applied, the sample maintains a roughly constant temperature until crystallization starts. Crystallization of the alloy results in the release of energy and corresponding sharp rise in temperature. The difference between the end of the capacitive discharge and the release of energy due to crystallization defines the crystallization time window. A metallic glass is suitable to make high aspect ratio parts if the crystallization time window is at least 100 ms. In some embodiments the viscosity of the metallic glass is between $10^2$-$10^4$ Pa-s.

In further aspects, the disclosure is directed to a metallic glass alloy feedstock. The metallic glass feedstock comprises metallic glass capable of resisting crystallization for at least 100 ms at a temperature where the viscosity is in the range of $10^0$ and $10^4$ Pa-s. In some embodiments, the metallic glass is capable of resisting crystallization for at least 100 ms at a temperature where the viscosity is in the range of $10^2$ and $10^4$ Pa-s. In certain variations, the feedstock has a substantially uniform cross section. The metallic glass alloy feedstock can be used in the methods described herein.

In additional aspects, the disclosure is directed to a shaped amorphous article formed from said feedstock using the methods described herein having features with aspect ratio of at least 10. In other aspects, the shaped amorphous article has features with a thickness of 2 mm or less. In some embodiments, the shaped amorphous article has features where the thickness is in the range of 0.5 to 2 mm.

In various embodiments, the metallic glass alloy composition is Zr—based, Ti—based, Al-based, Mg-based, Ce-based, La-based, Y-based, Fe-based, Ni—based, Co-based, Cu-based, Au-based, Pd-based, or Pt-based. In other embodiments, the metallic glass alloy composition is Ta—based, Hf-based, Pr-based, Nd-based, Gd-based, or Ca-based.

In still other embodiments, the metallic glass alloy composition has the following formula:

$$X_{100-a-b}Y_a Z_b \qquad \text{EQ. 1}$$

wherein:
X is Ni, Fe, Co or combinations thereof
Y is Cr, Mo, Mn, Nb, Ta or combinations thereof
Z is P, B, Si, C, Ge or combinations thereof
a is between 5 and 15 atomic %
b is between 15 and 25 atomic %.

In various embodiments, the metallic glass alloy composition is any Ni—based glass-forming alloy, including but not limited to, Ni—Cr—Nb—P—B, Ni—Cr—Ta—P—B, Ni—Cr—Mn—P—B, Ni—Mo—Nb—Mn—P—B, Ni—Mn—Nb—P—B, Ni—Cr—Mo—Si—B—P, and Ni—Fe—Si—B—P metallic glass alloy compositions.

In still other embodiments, the metallic glass alloy composition has the following formula:

$$Ni_{100-a-b-c-d}X_aY_bP_cZ_d \qquad \text{EQ. 2}$$

wherein:
X is Cr, Mo, Mn or combinations thereof
Y is Nb, Ta, Mn or combinations thereof
Z is B, Si or combinations thereof
a is between 3 and 15 atomic %
b is between 1 and 6 atomic %
c is between 12 and 20 atomic %
d is between 0.5 and 6 atomic %

In still yet other embodiments, the metallic glass alloy is selected from $Ni_{68.17}Cr_{8.65}Nb_{2.98}P_{16.42}B_{3.28}Si_{0.5}$, $Ni_{68.17}Cr_{8.65}Nb_{2.98}P_{15.92}B_{3.28}Si_1$, $Ni_{69}Cr_{10}Nb_{1.5}P_{18}B_{1.5}$, $Ni_{69}Cr_{9.5}Nb_2P_{17.5}B_2$, $Ni_{69}Cr_9Nb_2P_{17}B_{2.5}$, $Ni_{69}Cr_8Nb_{3.5}P_{16}B_{3.5}$, $Ni_{69}Cr_{7.5}Nb_4P_{15.5}B_4$, $Ni_{69}Cr_7Nb_{4.5}P_{15}B_{4.5}$, $Ni_{69}Cr_{8.75}Nb_{2.75}P_{16}B_{3.5}$, $Ni_{69}Cr_9Nb_{2.5}P_{15.5}B_4$, $Ni_{69}Cr_{9.25}Nb_{2.25}P_{15}B_{4.5}$, $Ni_{69}Cr_{9.5}Nb_2P_{14.5}B_5$, $Ni_{69}Cr_{9.75}Nb_{1.75}P_{14}B_{5.5}$, $Ni_{69}Cr_{10}Nb_{1.5}P_{13.5}B_6$, $Ni_{67.5}Co_{1.5}Cr_{8.5}Nb_3P_{16.5}B_3$, $Ni_{66}Co_3Cr_{8.5}Nb_3P_{16.5}B_3$, $Ni_{64}Co_5Cr_{8.5}Nb_3P_{16.5}B_3$, $Ni_{59}Co_{10}Cr_{8.5}Nb_3P_{16.5}B_3$, $Ni_{54}Co_{15}Cr_{8.5}Nb_3P_{16.5}B_3$, $Ni_{49}Co_{20}Cr_{8.5}Nb_3P_{16.5}B_3$, $Ni_{44}Co_{25}Cr_{8.5}Nb_3P_{16.5}B_3$, $Ni_{61.4}Co_{10}Cr_{5.52}Nb_{3.38}P_{16.67}B_{3.03}$, $Ni_{56.4}Co_{15}Cr_{5.52}Nb_{3.38}P_{16.67}B_{3.03}$, $Ni_{51.4}Co_{20}Cr_{5.52}Nb_{3.38}P_{16.67}B_{3.03}$, $Ni_{46.4}Co_{25}Cr_{5.52}Nb_{3.38}P_{16.67}B_{3.03}$, $Ni_{67.1}Cr_{10}Nb_{3.4}P_{18}Si_{1.5}$, $Ni_{66.1}Cr_{11}Nb_{3.4}P_{18}Si_{1.5}$, $Ni_{64.1}Cr_{13}Nb_{3.4}P_{18}Si_{1.5}$, $Ni_{62.1}Cr_{15}Nb_{3.4}P_{18}Si_{1.5}$, $Ni_{68.5}Cr_8Mn_3P_{17}B_3$, $Ni_{68.5}Cr_{7.5}Mn_3Mo_1P_{16.5}B_3$, $Ni_{68.5}Cr_9Ta_3P_{16.5}B_3$, $Ni_{68.5}Cr_9Ta_3P_{16.25}B_{3.25}$, $Ni_{68.5}Cr_9Ta_3P_{16}B_{3.5}$, $Ni_{68.5}Cr_9Ta_3P_{15.5}B_4$, $Ni_{68.5}Cr_9Ta_3P_{15}B_{4.5}$, $Ni_{69.5}Cr_8Ta_3P_{16.25}B_{3.25}$, $Ni_{68.5}Cr_9Ta_3P_{16.25}B_{3.25}$, $Ni_{67.5}Cr_{10}Ta_3P_{16.25}B_{3.25}$, $Ni_{68.5}Cr_{10}Ta_2P_{16.25}B_{3.25}$, $Ni_{68.5}Cr_{9.5}Ta_{2.5}P_{16.25}B_{3.25}$, and $Ni_{68.5}Cr_{8.5}Ta_{3.5}P_{16.25}B_{3.25}$.

In still yet other embodiments, the metallic glass alloy crystallizes at a temperature $T_x$ that is at least 45° C. higher than its glass transition temperature $T_g$ when heated by a constant heating rate of 0.67° C./s.

In still yet other embodiments the disclosure is directed to a high-aspect-ratio article. The article has at least one featuring with an aspect ratio of at least 10. In some embodiments, the article has at least one feature with a thickness of 2 mm or less. In further embodiments, the article has at least one feature with a thickness in the range of 0.5 to 2 mm shaped from a metallic glass as described herein.

In still yet other embodiments, the high-aspect-ratio article is a component of a consumer electronics device, a watch component, a medical implant, a dental prosthetic, a ferromagnetic core, a sporting good, or a luxury good.

BRIEF DESCRIPTION OF THE DRAWINGS

The description will be more fully understood with reference to the following figures and data graphs, which are presented as various embodiments of the disclosure and should not be construed as a complete recitation of the scope of the disclosure.

DETAILED DESCRIPTION

Figure 1:
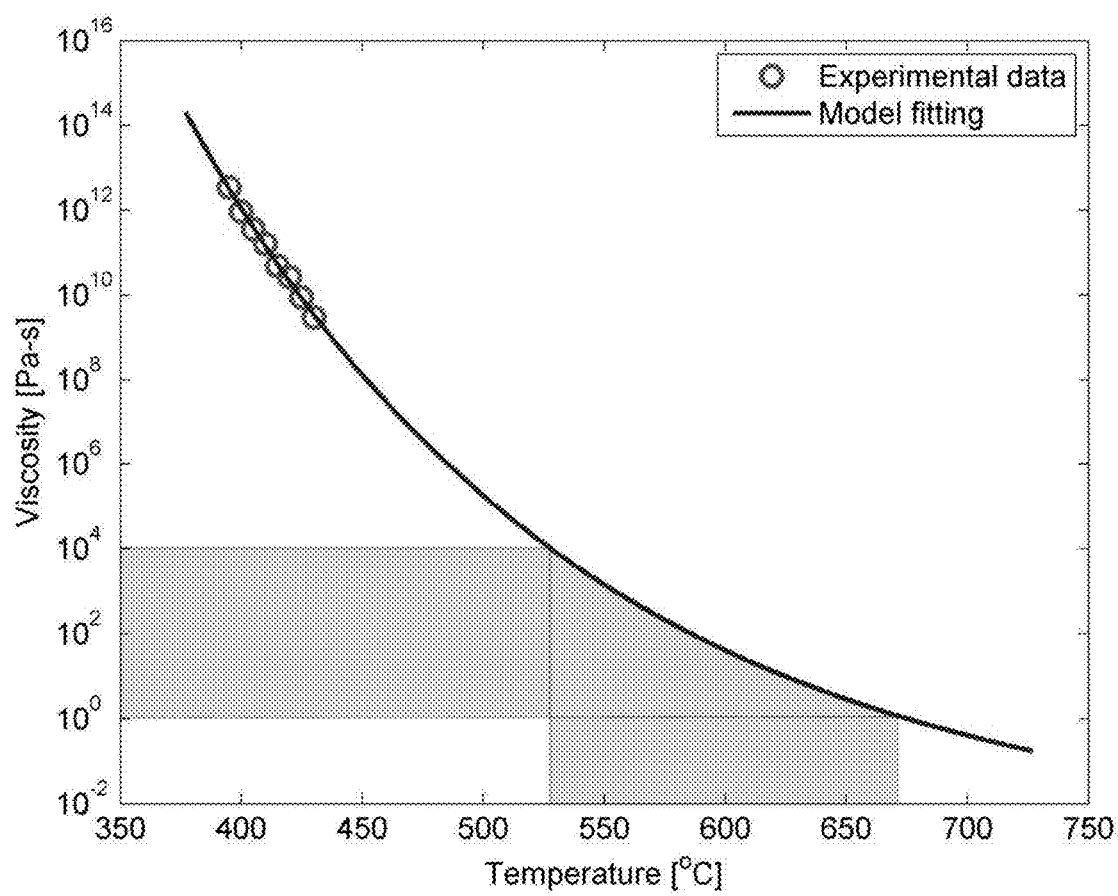
FIG. 1 provides a plot of experimental data and model fitting for the temperature dependent viscosity of $Ni_{68.17}Cr_{8.65}Nb_{2.98}P_{16.42}B_{3.28}$ metallic glass.

The present disclosure may be understood by reference to the following detailed description, taken in conjunction with the drawings as described below. It is noted that, for purposes of illustrative clarity, certain elements in various drawings may not be drawn to scale, may be represented schematically or conceptually, or otherwise may not correspond exactly to certain physical configurations of embodiments.

The present disclosure is directed to methods and materials that allow for the use of RCDF to shape high aspect ratio articles. The articles prepared in this manner exhibit finished surfaces that are substantially free from cosmetic defects and/or flaws.

As used herein, "high aspect ratio articles" refer to articles having aspect ratios (defined as the longest dimension of a 3D object article divided over the shortest dimension of a 3D object) of at least 10. In some embodiments, the article has a thickness (the shortest dimension of a 3D object) on the order of 2 mm or less. In other embodiments, the article has at least one feature with a thickness of 2 mm or less. In further embodiments, the article has at least one feature with a thickness in the range of 0.5 to 2 mm. It will be understood to those in the art that high aspect ratios articles refer to articles having at least one feature with a high aspect ratio. A feature can be any portion of an article, and is not limited to the total size of the article. In various embodiments, the crystallization time of an amorphous alloy is sufficiently long to allow the amorphous alloy to occupy the high aspect ratio feature without defects or incongruities.

RCDF Process

In RCDF, a quantum of electrical energy is discharged through a metallic glass sample having a uniform cross-section. The sample is rapidly and uniformly heated to a processing temperature between the glass transition temperature of the metallic glass and the equilibrium melting temperature of the metallic glass alloy. A deformational force is applied to the heated and softened feedstock either during or after the rapid uniform heating. The sample is shaped and cooled to form a metallic glass article.

As used herein, a "uniform cross-section" includes minor surface inconsistencies (e.g. <5% of a cross-sectional diameter) in the cross-section. As used herein, "uniformly heated" refers to heating the feedstock core to substantially the same temperature (e.g. within 10% of the temperature in Kelvin). It is contemplated that uniform heating refers to the feedstock core, and very small regions in the feedstock sufficiently close to the contact points with the electrodes (i.e. in some embodiments within 5 mm, and in other embodiments within 1 mm) may have temperatures above or below the mean temperature of the core of the feedstock.

The article can be shaped by any shaping method known in the art. For example, any deformational force can be applied simultaneously or subsequently to heating in order to shape the heated sample into an article. Non-limiting examples of different shaping techniques may include molding, forging, casting, and blow molding, among others.

The RCDF process involves rapidly discharging electrical current across a metallic glass feedstock via electrodes in contact with feedstock in order to rapidly and uniformly heat the feedstock to a temperature conducive for viscous flow. The RCDF process has certain internal time scales, the first of which is the duration of the heating pulse, $t_h$, which is the time to heat a metallic glass feedstock to a desired process temperature above the glass transition. The second time scale is the duration of the shaping process, $t_s$. This is the available time during which the heated feedstock may be shaped to the desired final shape without crystallizing the metallic glass. Another time scale, $t_c$, is the amount of time to cool the fully shaped part to below $T_g$. Adding these time scales together gives the duration of the RCDF process as $t_{RCDF} = t_h + t_s + t_c$. It is critical for the heating and shaping of the initial unprocessed metallic glass ("feedstock") to be completed before the amorphous feedstock crystallizes. Therefore, the crystallization time $t_{cryst}$ must be longer than $t_{RCDF}$ the time it takes for the RCDF process to heat, shape and cool the feedstock sample (i.e. $t_{cryst} > t_{RCDF}$).

For high aspect ratio articles, the duration of the RCDF process is dominated by the duration of the shaping process. The target process temperature range in RCDF is the range of temperatures associated with a viscosity in the range of $10^0$ to $10^4$ Pa-s, or alternatively in the range of $10^1$ to $10^3$ Pa-s, or in the range of $10^2$ to $10^4$ Pa-s. As disclosed in U.S. Patent Publications 2012/0103478 and 2009/0236017, each of which is incorporated herein by reference in its entirety, if the viscosity is higher than about $10^4$ Pa-s, the metallic glass alloy may not fill a mold by injection molding, or the injection pressure required to enable complete filling may be too high causing damage to the mold. On the other hand, if the viscosity is substantially lower than $10^0$ Pa-s, it may be too low to sustain stable flow such that flow instabilities would develop causing voids or defects in the final article.

The viscosity of the metallic glass depends strongly on temperature. Most metallic glasses have a predictable dependence between temperature and viscosity. Specifically, the viscosity of the BMG drops by about 15 orders of magnitude when the temperature rises from the glass transition to above the melting point of the alloy following a predictable function. This means that the forming conditions (pressure and time) required to shape a metallic glass depends critically on the temperature under which shaping is being performed.

To successfully shape high-aspect-ratio articles that are free of structural and cosmetic defects, shaping should be performed at a strain rate low enough to keep the flow inertia force low compared to the flow front surface tension and avoid flow-front breakup (Weber instabilities), which leads to surface defects such as cellularization, roughening, and flow lines. Generally, when shaping high aspect ratio articles, processing strain rates should not exceed 100 s$^{-1}$.

Based on these processing parameters, the lower limit for $t_s$ may be estimated as the ratio between the lower limit of total strain, which is essentially the aspect ratio, and the higher limit of strain rate. For example, in the current disclosure, the lowest limit in aspect ratio is about 10 and the highest limit in strain rate is about 100 s$^{-1}$, thus the lower bound for the shaping time may be 0.1 s or 100 ms. As shown below, such shaping time is significantly larger than both $t_h$ and $t_c$.

The heating time may be estimated as follows. In the RCDF process, the circuit capacitance typically ranges between 0.1 and 2 F, and a total resistance (metallic glass feedstock resistance plus system resistance) between 1 and 5 mΩ, is typical. Therefore, the heating time $t_h$, which is essentially equivalent to the rise time for the current discharge and may be roughly approximated by the product between capacitance and resistance, may be on the order of few ms and not significantly more than 10 ms. Hence, $t_h \ll t_s$.

The cooling time may be estimated as follows. The time to cool the centerline of an article with a lateral dimension 2L by about 63% of the temperature difference (difference between process temperature and mold temperature) may be approximated by the thermal relaxation (Fourier) time $\tau_{th} = L^2/a$, where L is the article half-thickness, and may be on the order of 0.5 mm, and a is the metallic glass thermal diffusivity, which ranges between $1 \times 10^{-6}$ and $5 \times 10^{-6}$ m$^2$/s for most metallic glasses. Therefore typical thermal relaxation times for such metallic glass articles may be on the order of $\tau_{th}$ about 100 ms. But these relaxation times represent cooling times to about 63% of the total temperature difference. The total temperature difference in RCDF is typically on the order of 500-600 degrees when cooling from a process temperature where the viscosity is between $10^0$ and $10^4$ Pa-s (or alternatively in the range of $10^1$ and $10^3$ Pa-s or in the range of $10^2$ and $10^4$ Pa-s) to the temperature of the mold, which is typically held at room temperature. The requirement for bypassing crystallization in the RCDF process is to cool the melt to just below the process temperature, but not necessarily below $T_g$, i.e. only by about 100-200 degrees, so the cooling time is only a small fraction of $\tau_{th}$, that is, only a small fraction of about 100 ms. For example, the cooling time may be 20 ms, which is much smaller than the minimum shaping time, i.e. 100 ms.

Accordingly, some embodiments are directed to a process for shaping high-aspect ratio articles using RCDF. A metallic glass is selected wherein $t_{cryst} > t_s > 100$ ms at a temperature where the viscosity of the metallic glass is between $10^0$ and $10^4$ Pa-s, or alternatively in the range of $10^1$ and $10^3$ Pa-s, or in the range of $10^2$ and $10^4$ Pa-s. A feedstock of the metallic glass having a substantially uniform cross-section is formed. A quantum of electrical energy is applied to the feedstock using an RCDF system to heat the feedstock to a processing window at a temperature where the viscosity is between $10^0$ and $10^4$ Pa-s, or alternatively in the range of $10^1$ and $10^3$ Pa-s, or in the range of $10^2$ and $10^4$ Pa-s. The heated feedstock is shaped into a high-aspect-ratio article. The shaped article is cooled to a temperature below the glass transition temperature of the metallic glass sufficiently fast to avoid crystallization of the metallic glass.

In some embodiments the shaped amorphous article has features with aspect ratio of at least 10. In other embodiments, the shaped amorphous article has features with a thickness of 2 mm or less. In yet other embodiments, the shaped amorphous article has features with a thickness in the range of 0.5 to 2 mm. The shaping step may take the form of any application of deformational force applied simultaneously or subsequently to shape the heated sample into an article. Examples of such shaping techniques may include molding, forging, casting, and blow molding, among others.

In some embodiments, the shaped article is a component of a consumer electronics device, a watch component, a medical implant, a dental prosthetic, a ferromagnetic core, a sporting good, or a luxury good.

Screening for RCDF Alloys Satisfying the Criterion Set Forth Herein

The present disclosure is also directed to methods of screening metallic glass-forming alloy systems to assess the suitability of specific alloys for being shaped into high-aspect ratio articles substantially free of cosmetic defects and flaws using RCDF.

In some such embodiments, the $t_{cryst}$ time window is measured by heating a sample of the metallic glass by capacitive discharge using the RCDF method while concurrently measuring the temperature of the sample. Once the capacitive discharge is completed, the sample attains and maintains a roughly constant temperature (which also can be referred to as the "process temperature") until crystallization of the feedstock occurs, marked by releasing energy and causing the temperature to rise sharply, thereby designating $t_{cryst}$. Knowledge of the viscosity function of temperature for the specific alloy (or for an alloy of very similar composition), would enable those skilled in the art to determine whether the viscosity at the process temperature is within the range of viscosities described herein.

RCDF Alloy Systems

The present disclosure is also directed to metallic glass-forming alloy systems possessing specific stability criteria such that they are capable of being shaped into high-aspect ratio articles substantially free of cosmetic defects and flaws using RCDF. More particularly, in many variations the disclosure is directed to a metallic glass alloy capable of resisting crystallization for at least 100 ms at a temperature above the glass transition where the viscosity is in the range of $10^0$ and $10^4$ Pa-s, or alternatively in the range of $10^1$ and $10^3$ Pa-s, or alternatively in the range of $10^2$ and $10^4$ Pa-s.

The metallic glass alloy composition is Zr—based, Ti—based, Ta—based, Y-based, Hf-based, Ni—based, Pd-based, Pt-based, Fe-based, Ni—based, Co-based, Cu-based, Au-based, Al-based, La-based, Ce-based, Pr-based, Ng-based, Gd-based, Mg-based, or Ca-based.

In certain embodiments, the metallic glass alloy composition is a Zr—based metallic glass alloy composition that may include elements selected from the group consisting of Ti, Ni, Cu, Be, Hf, Nb, V, Al, Sn, Ag, Pd, Fe, Co, and Cr.

In certain embodiments, the metallic glass alloy composition is Fe-based metallic glass alloy composition that may include elements selected from the group consisting of Co, Ni, Mo, Cr, P, C, B, Si, Al, Zr, W, Mn, Y, and Er.

In certain embodiments, the metallic glass alloy composition is Ni—based metallic glass alloy composition that may include elements selected from the group consisting of Co, Fe, Cu, Mo, Cr, P, B, Si, Sn, Nb, Ta, V, and Mn.

In certain embodiments, the metallic glass alloy composition is Cu-based metallic glass alloy composition that may include elements selected from the group consisting of Zr, Ti, Ni, Au, Ag, Hf, Nb, V, Si, Sn, and P.

In certain embodiments, the metallic glass alloy composition is Au-based metallic glass alloy composition that may include elements selected from the group consisting of Cu, Si, Ag, Pd, Pt, Ge, Y, and Al.

In certain embodiments, the metallic glass alloy composition is Pd-based metallic glass alloy composition that may include elements selected from the group consisting of Pt, Ni, Cu, P, Si, Ge, Ag, Au, Fe, and Co.

In certain embodiments, the metallic glass alloy composition is Pt-based metallic glass alloy composition that may include elements selected from the group consisting of Pd, Ni, Cu, P, Si, Ge, Ag, Au, Fe, and Co.

In still other embodiments, the metallic glass alloy composition has the following formula:

$$X_{100-a-b}Y_aZ_b \qquad \text{EQ. 1}$$

wherein:
X is Ni, Fe, Co or combinations thereof
Y is Cr, Mo, Mn, Nb, Ta or combinations thereof
Z is P, B, Si, C, Ge or combinations thereof
a is between 5 and 15 atomic %
b is between 15 and 25 atomic %.

In various embodiments, the metallic glass alloy composition is any Ni—based glass-forming alloy, including but not limited to, Ni—Cr—Nb—P—B, Ni—Cr—Ta—P—B, Ni—Cr—Mn—P—B, Ni—Mo—Nb—Mn—P—B, Ni—Mn—Nb—P—B, Ni—Cr—Mo—Si—B—P, and Ni—Fe—Si—B—P metallic glass alloy compositions.

In still other embodiments, the metallic glass alloy composition has the following formula:

$$Ni_{100-a-b-c-d}X_aY_bP_cZ_d \qquad \text{EQ. 2}$$

wherein:
X is Cr, Mo, Mn or combinations thereof
Y is Nb, Ta, Mn or combinations thereof
Z is B, Si or combinations thereof
a is between 3 and 15 atomic %
b is between 1 and 6 atomic %
c is between 12 and 20 atomic %
d is between 0.5 and 6 atomic %.

In various additional embodiments, the metallic glass alloy composition is selected from $Ni_{68.17}Cr_{8.65}Nb_{2.98}P_{16.42}B_{3.28}Si_{0.5}$, $Ni_{68.17}Cr_{8.65}Nb_{2.98}P_{15.92}B_{3.28}Si_{1.1}$, $Ni_{69}Cr_{10}Nb_{1.5}P_{18}B_{1.5}$, $Ni_{69}Cr_{9.5}Nb_2P_{17.5}B_2$, $Ni_{69}Cr_9Nb_{2.5}P_{17}B_{2.5}$, $Ni_{69}Cr_8Nb_{3.5}P_{16}B_{3.5}$, $Ni_{69}Cr_{7.5}Nb_4P_{15.5}B_4$, $Ni_{69}Cr_7Nb_{4.5}P_{15}B_{4.5}$, $Ni_{69}Cr_{8.75}Nb_{2.75}P_{16}B_{3.5}$, $Ni_{69}Cr_8Nb_{2.5}P_{15.5}B_4$, $Ni_{69}Cr_{9.25}Nb_{2.25}P_{15}B_{4.5}$, $Ni_{69}Cr_{9.5}Nb_2P_{14.5}B_3$, $Ni_{69}Cr_{9.75}Nb_{1.75}P_{14}B_{5.5}$, $Ni_{69}Cr_{10}Nb_{1.5}P_{13.5}B_6$, $Ni_{67.5}Co_{1.5}Cr_{8.5}Nb_3P_{16.5}B_3$, $Ni_{66}Co_3Cr_{8.5}Nb_3P_{16.5}B_3$, $Ni_{64}Co_5Cr_{8.5}Nb_3P_{16.5}B_3$, $Ni_{59}Co_{10}Cr_{8.5}Nb_3P_{16.5}B_3$, $Ni_{54}Co_{15}Cr_{8.5}Nb_3P_{16.5}B_3$, $Ni_{49}Co_{20}Cr_{8.5}Nb_3P_{16.5}B_3$, $Ni_{44}Co_{25}Cr_{8.5}Nb_3P_{16.5}B_3$, $N_{61.4}Co_{10}Cr_{5.52}Nb_{3.38}P_{16.67}$, $Ni_{56.4}Co_{15}Cr_{5.52}Nb_{3.38}P_{16.67}B_{3.03}$, $Ni_{51.4}Co_{20}Cr_{5.52}Nb_{3.38}P_{16.67}B_{3.03}$, $Ni_{46.4}Co_{25}Cr_{5.52}Nb_{3.38}P_{16.67}B_{3.03}$, $Ni_{67.1}Cr_{10}Nb_{3.4}P_{18}Si_{1.5}$, $Ni_{66.1}Cr_{11}Nb_{3.4}P_{18}Si_{1.5}$, $Ni_{64.1}Cr_{13}Nb_{3.4}P_{18}Si_{1.5}$, $Ni_{62.1}Cr_{15}Nb_{3.4}P_{18}Si_{1.5}$, $Ni_{68.5}Cr_{8.5}Mn_3P_{17}B_3$, $Ni_{68.5}Cr_{7.5}Mn_3Mo_1P_{16.5}B_3$, $Ni_{68.5}Cr_9Ta_3P_{16.5}B_3$, $Ni_{68.5}Cr_9Ta_3P_{16.25}B_{3.25}$, $Ni_{68.5}Cr_9Ta_3P_{16.25}B_{3.5}$, $Ni_{68.5}Cr_9Ta_3P_{15.5}B_4$, $Ni_{68.5}Cr_8Ta_3P_{15}B_{4.5}$, $Ni_{69.5}Cr_8Ta_3P_{16.25}B_{3.25}$, $Ni_{68.5}Cr_9Ta_3P_{16.25}B_{3.25}$, $Ni_{67.5}Cr_{10}Ta_3P_{16.25}B_{3.25}$, $Ni_{68.5}Cr_{10}Ta_2P_{16.25}B_{3.25}$, $Ni_{68.5}Cr_{9.5}Ta_{2.5}P_{16.25}B_{3.25}$, and $Ni_{68.5}Cr_{8.5}Ta_{3.5}P_{16.25}B_{3.25}$.

Correlation with ΔT

The metallic glass alloys that satisfy the criterion $t_{cryst}>t_s>100$ ms within the temperature range associated with a viscosity range of $10^0$ and $10^4$ Pa-s, or alternatively in the range of $10^1$ and $10^3$ Pa-s, or alternatively in the range of $10^2$ and $10^4$ Pa-s, generally demonstrate a relatively high stability against crystallization. The present disclosure provides metallic glass alloys that are stable against crystallization when held at temperatures associated with viscosities in the range of $10^0$ and $10^4$ Pa-s, or alternatively in the range of $10^1$ and $10^3$ Pa-s, or alternatively in the range of $10^2$ and $10^4$ Pa-s, such that $t_{cryst}>100$ ms at those temperatures, and are also stable against crystallization when heated at a constant rate above $T_g$, such that $\Delta T=T_x-T_g$, where $T_x$ is the crystallization temperature, is relatively large. Likewise, metallic glass alloys demonstrating insufficient stability against crystallization at the disclosed temperatures also demonstrate limited ΔT when heated at constant rate above $T_g$. Accordingly, in yet other embodiments, metallic glasses capable of being shaped into high-aspect ratio articles using RCDF may crystallize at a temperature $T_x$ that is at least 45° C. higher than their glass transition temperature $T_g$ when heated by a constant heating rate of 0.67° C./s.

EXAMPLES

The following examples describe in detail preparation and characterization of alloys and methods disclosed herein. It will be apparent to those of ordinary skill in the art that many modifications, to both materials and methods, may be practiced.

Example 1: Screening of Ni—Based Alloys

To explore the processing window and the RCDF shaping capabilities as a function of composition, the family of Ni—Cr—Nb—P—B glass-forming alloys disclosed in U.S. patent application Ser. No. 13/592,095, entitled "Bulk Nickel-Based Chromium and Phosphorus Bearing Metallic Glasses", filed on Aug. 22, 2012, and Ser. No. 14/067,521, entitled "Bulk Nickel-Based Chromium and Phosphorus Bearing Metallic Glasses with High Toughness", filed on Oct. 30, 2013, the disclosures of which are incorporated herein by reference in their entirety, was investigated. Experimental data and model fitting for the viscosity of $Ni_{68.17}Cr_{8.65}Nb_{2.98}P_{16.42}B_{3.28}Si_{0.5}$ metallic glass are presented in FIG. 1. Ni—Cr—Nb—P—B metallic glasses and generally metallic glasses whose composition is governed by EQ. 2 were expected to exhibit viscosity similar to $Ni_{68.17}Cr_{8.65}Nb_{2.98}P_{16.42}B_{3.28}Si_{0.5}$ metallic glass. As shown by the shaded area in FIG. 1, $Ni_{68.17}Cr_{8.65}Nb_{2.98}P_{16.42}B_{3.28}Si_{0.5}$ metallic glass exhibits a viscosity within the desirable viscosity range of $10^0$ and $10^4$ Pa-s at temperatures in the range of 525-675° C.

Figure 2:
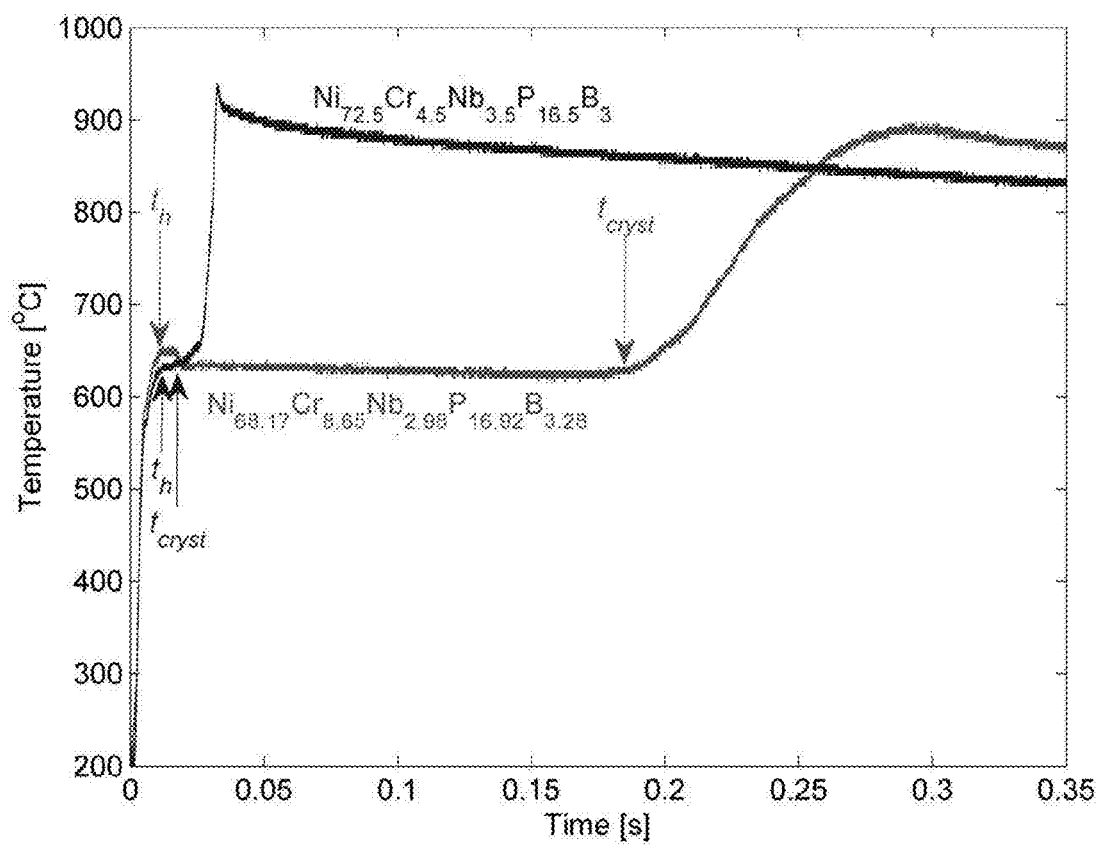
FIG. 2 provides RCDF heating curves for metallic glass alloys $Ni_{72.5}Cr_{4.5}Nb_{3.5}P_{16.5}B_3$ and $Ni_{68.17}Cr_{8.65}Nb_{2.98}P_{16.92}B_{3.28}$.

The temperature vs. time curves following capacitive discharge heating of samples of metallic glasses $Ni_{72.5}Cr_{4.5}Nb_{3.5}P_{16.5}B_3$ and $Ni_{68.17}Cr_{8.65}Nb_{2.98}P_{16.92}B_{3.28}$ are presented in FIG. 2. The heating time $t_h$ and crystallization time $t_{cryst}$ for each alloy are designated. Both metallic glasses underwent heating at roughly the same $t_h$ but crystallized at very different $t_{cryst}$. Specifically, both metallic glasses were heated for $t_h$ of about 10 ms, but metallic glass $Ni_{72.5}Cr_{4.5}Nb_{3.5}P_{16.5}B_3$ crystallized at $t_{cryst}$ of about 30 ms while metallic glass $Ni_{68.17}Cr_{8.65}Nb_{2.98}P_{16.92}B_{3.28}$ crystallized at $t_{cryst}$ of about 200 ms. Therefore, metallic glass $Ni_{72.5}Cr_{4.5}Nb_{3.5}P_{16.5}B_3$ did not meet the criterion $t_{cryst}>t_s>100$ ms set forth in this disclosure, while metallic glass $Ni_{68.17}Cr_{8.65}Nb_{2.98}P_{16.92}B_{3.28}$ did meet the criterion. Consequently, metallic glass $Ni_{72.5}Cr_{4.5}Nb_{3.5}P_{16.5}B_3$ may not be shaped into high aspect ratio articles by RCDF according to the methods disclosed herein, while alloy $Ni_{68.17}Cr_{8.65}Nb_{2.98}P_{16.92}B_{3.28}$ may be shaped into high aspect ratio articles by RCDF.

Figure 3:
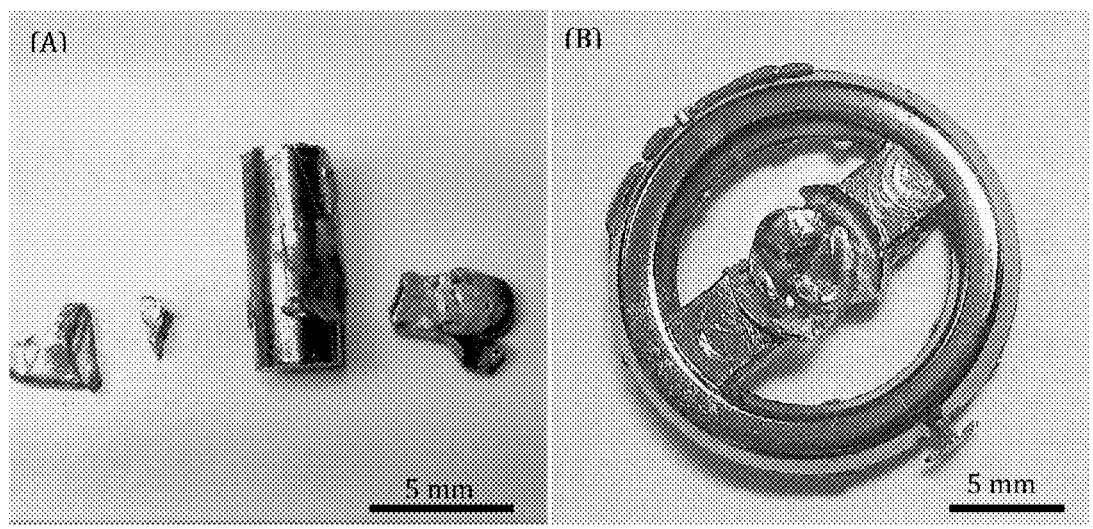
FIG. 3 provides images of parts produced in two RCDF molding experiments using metallic glass alloys $Ni_{72.5}Cr_{4.5}Nb_{3.5}P_{16.5}B_3$ (A), and $Ni_{68.17}Cr_{8.65}Nb_{2.98}P_{16.92}B_{3.28}$ (B).

FIG. 3A demonstrates that metallic glass $Ni_{72.5}Cr_{4.5}Nb_{3.5}P_{16.5}B_3$ could not be shaped into a high aspect ratio part having a planar toroidal shape because the shaping process was discontinuous and led to loose molded parts that have crystallized. In contrast, FIG. 3B demonstrates that metallic glass $Ni_{68.17}Cr_{8.65}Nb_{2.98}P_{16.92}B_{3.28}$ could be successfully shaped into a high aspect ratio part having a planar toroidal shape. The part in FIG. 3B filled the mold entirely, and had an amorphous structure as verified by x-ray diffraction. The molded part contained features having aspect ratio greater than 10 and thickness less than 1 mm.

Figure 4A:
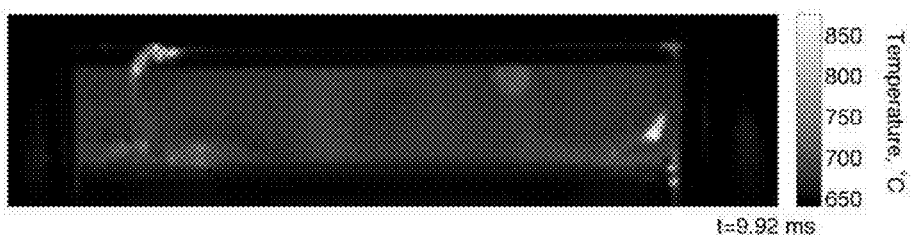
FIG. 4 provides infrared images associated with RCDF heating for metallic glass alloys $Ni_{72.5}Cr_{4.5}Nb_{3.5}P_{16.5}B_3$ (A-D), and $Ni_{68.17}Cr_{8.65}Nb_{2.98}P_{16.92}B_{3.28}$ (E-H). Specifically, FIG. 4A provides infrared images associated with RCDF heating for metallic glass alloy $Ni_{72.5}Cr_{4.5}Nb_{3.5}P_{16.5}B_3$ after 9.92 ms have elapsed, FIG. 4B after 18.7 ms, FIG. 4C after 27.5 ms, and FIG. 4D after 39.2 ms.
FIG. 4E provides infrared images associated with RCDF heating for metallic glass alloy $Ni_{68.17}Cr_{8.65}Nb_{2.98}P_{16.92}B_{3.28}$ after 11.46 ms have elapsed, FIG. 4F after 50.48 ms, FIG. 4G after 118.77 ms, and FIG. 4H after 138.28 ms.
Figure 4B:
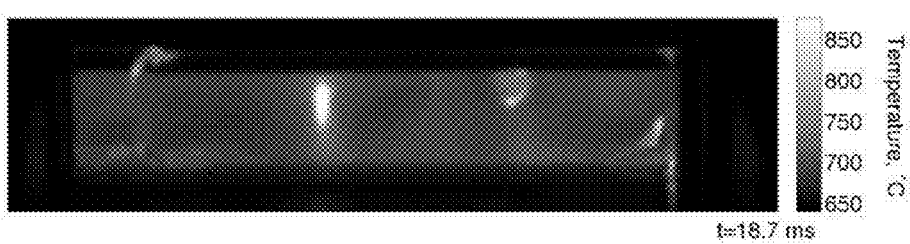
Figure 4C:
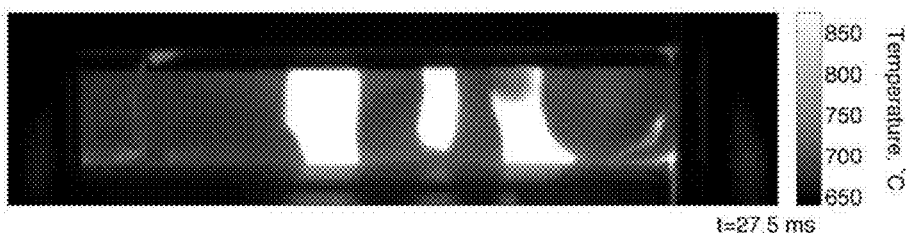
Figure 4D:
Figure 4E:
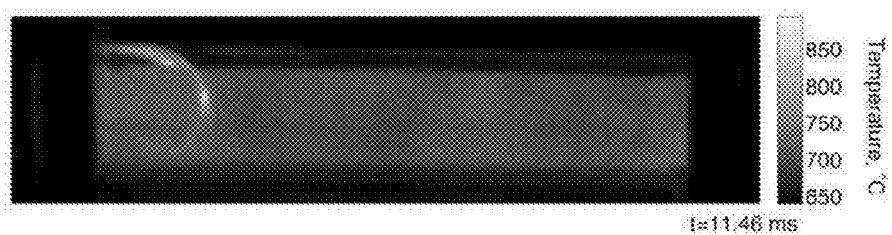
Figure 4F:
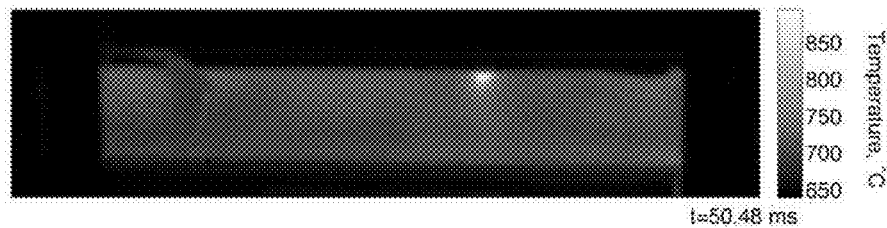
Figure 4G:
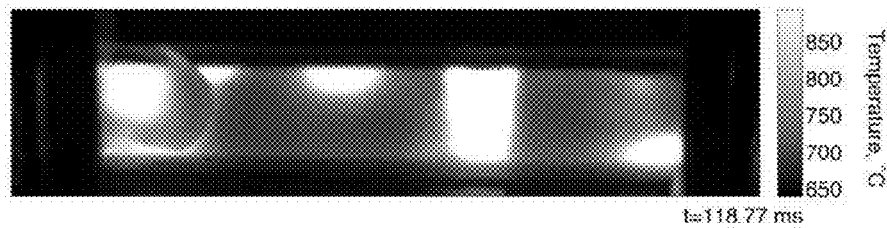
Figure 4H:
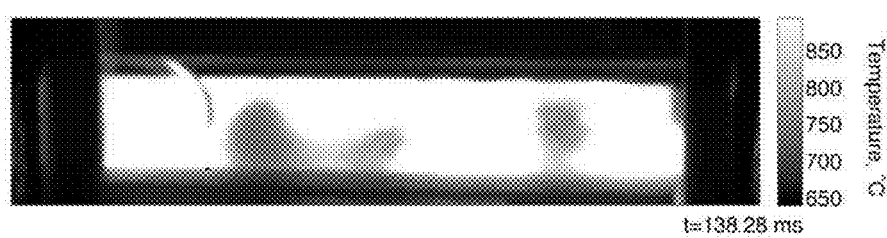

Infrared images associated with the RCDF heating of metallic glass alloys $Ni_{72.5}Cr_{4.5}Nb_{3.5}P_{16.5}B_3$ and $Ni_{68.17}Cr_{8.65}Nb_{2.98}P_{16.92}B_{3.28}$ showing the spatial evolution of crystallization are presented in FIGS. 4A to 4H. The infrared images, which are qualitatively consistent with the pyrometer measurements performed at a single point of the bulk sample, show that the crystallization, marked by a rapid rise in temperature (bright color) associated with the release of the crystallization enthalpy, occurred much sooner in $Ni_{72.5}Cr_{4.5}Nb_{3.5}P_{16.5}B_3$ than in $Ni_{68.17}Cr_{8.65}Nb_{2.98}P_{16.92}B_{3.28}$. Specifically, the infrared images demonstrated that at a plateau temperature of about 650° C., metallic glass alloy $Ni_{72.5}Cr_{4.5}Nb_{3.5}P_{16.5}B_3$ crystallized completely at 39.2 ms (FIG. 4D) while alloy $Ni_{68.17}Cr_{8.65}Nb_{2.98}P_{16.92}B_{3.28}$ did not crystallize completely even after 138.28 ms have elapsed (FIG. 4H).

The RCDF heating curves were produced for four metallic glass alloys heated to different temperatures, achieved by adjusting the energy discharge through various samples. The four metallic glass alloys are $Ni_{68.17}Cr_{8.65}Nb_{2.98}P_{16.92}B_{3.28}$, $Ni_{68.5}Cr_9Nb_3P_{15.5}B_3Si_1$, $Ni_{71.4}Cr_{5.52}Nb_{3.38}P_{16.67}B_{3.03}$, and $Ni_{72.5}Cr_{4.5}Nb_{3.5}P_{16.5}B_3$. The crystallization times obtained for each alloy by RCDF heating to various plateau temperatures within the range of 525-675° C. are listed in Table 1. At each plateau temperature, the time to crystallization $t_{cryst}$ was recorded and plotted in Time-Temperature-Transformation (TTT) plot in FIG. 5. The temperature range of 525-675° C. where the viscosity is expected to be within the range of $10^0$ and $10^4$ Pa-s is highlighted by a shaded band in FIG. 5. Two metallic glass alloys, $Ni_{68.17}Cr_{8.65}Nb_{2.98}P_{16.92}B_{3.28}$ and $Ni_{68.5}Cr_9Nb_3P_{15.5}B_3Si_1$, demonstrated time windows for shaping equal to or greater than about 100 ms within this temperature (and viscosity) range, and thus met criterion set forth in the current disclosure. Two other metallic glass alloys, $Ni_{71.4}Cr_{5.52}Nb_{3.38}P_{16.67}B_{3.03}$ and $Ni_{72.5}Cr_{4.5}Nb_{3.5}P_{16.5}B_3$, demonstrated time windows within this temperature (and viscosity) range that were considerably smaller than 100 ms, and therefore did not meet the criterion of the present disclosure.

Example 2: Assessing a Cu-Based Alloy

Figure 6:
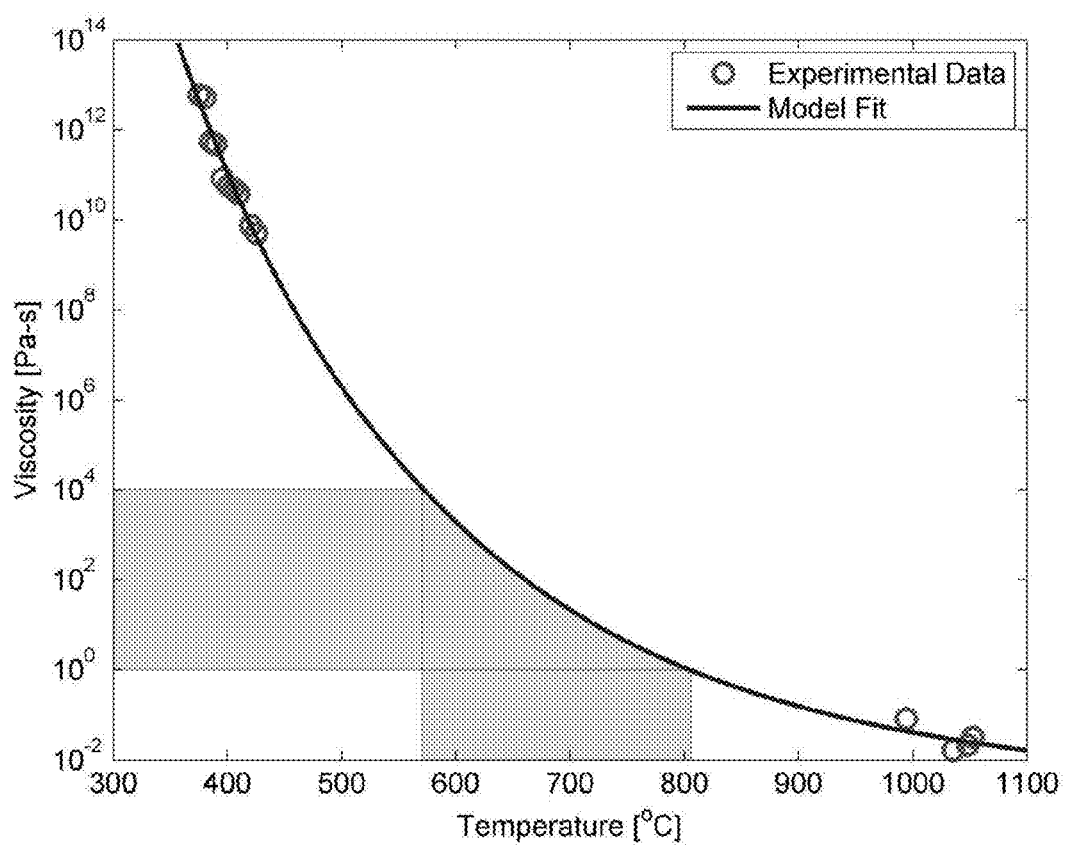
FIG. 6 provides a plot of experimental data and model fitting for the temperature dependent viscosity of $Cu_{47}Ti_{34}Zr_{11}Ni_8$ metallic glass.
Figure 7:
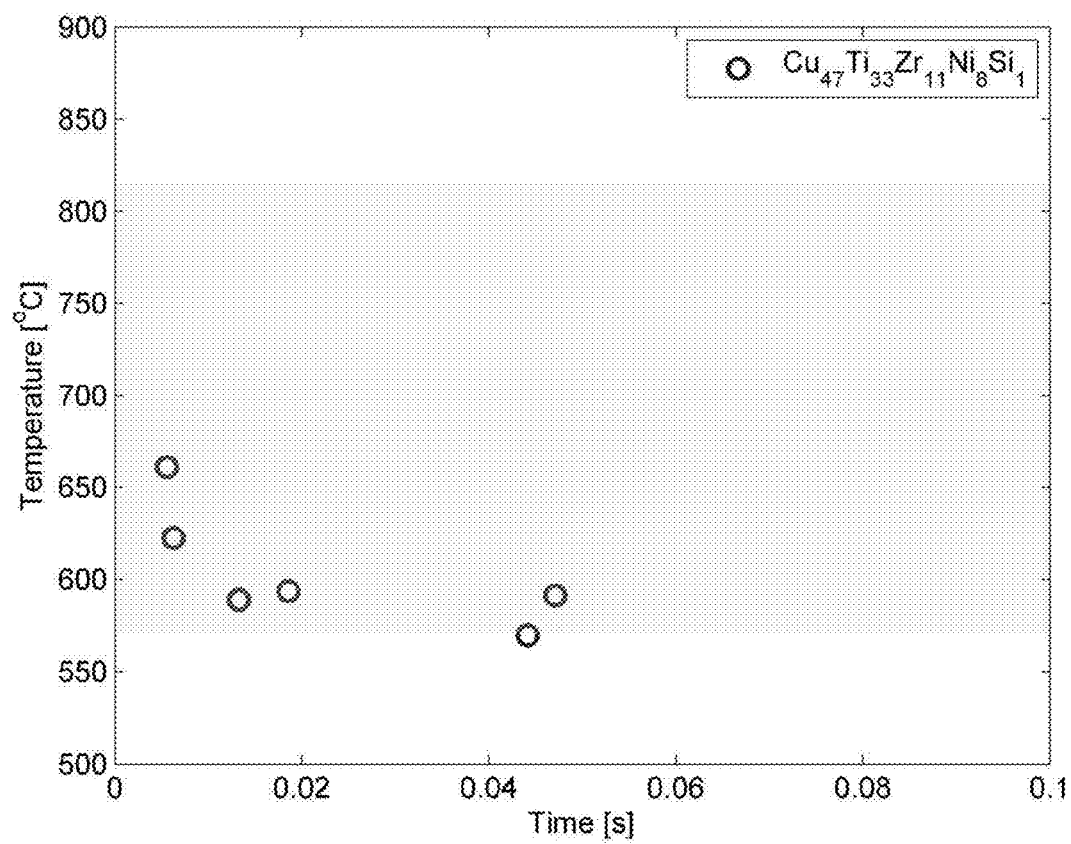
FIG. 7 provides a Time-Temperature-Transformation (TTT) plot for metallic glass alloy $Cu_{47}Ti_{33}Zr_{11}Ni_8Si_1$.

To further explore the processing window and the RCDF shaping capabilities, a Cu—Ti—Zr—Ni glass-forming alloy was also investigated. Experimental data and model fitting for the viscosity of $Cu_{47}Ti_{34}Zr_{11}Ni_8$ metallic glass is presented in FIG. 6. Cu—Ti—Zr—Ni metallic glasses in general were expected to exhibit viscosity similar to $Cu_{47}Ti_{34}Zr_{11}Ni_8$ metallic glass. As shown by the shaded area in FIG. 6, $Cu_{47}Ti_{34}Zr_{11}Ni_8$ metallic glass exhibited a viscosity within the desirable viscosity range of $10^0$ and $10^4$ Pa-s at temperatures in the range of 570-810° C. The RCDF heating curves were produced for metallic glass $Cu_{47}Ti_{33}Zr_{11}Ni_8Si_1$ alloy heated to different temperatures, achieved by adjusting the energy discharge through various samples. The crystallization times obtained by RCDF heating to various plateau temperatures within the range of 570-810° C. are listed in Table 2. At each plateau temperature, the time to crystallization $t_{cryst}$ was recorded and plotted in Time-Temperature-Transformation (TTT) plot in FIG. 7. The temperature range of 570-810° C. where the viscosity was expected to be within the range of $10^0$ and $10^4$ Pa-s is highlighted by a shaded band in FIG. 7. This metallic glass alloy demonstrated time windows within this temperature (and viscosity) range that were considerably smaller than 100 ms, and therefore did not meet the criterion of the present disclosure.

Example 3: Correlation with ΔT

Differential scanning calorimetry was also performed for these alloys. The metallic glass alloys were scanned to above $T_g$ at a constant heating rate of 0.67° C./s. The differential calorimetry scans for $Ni_{68.17}Cr_{8.65}Nb_{2.98}P_{16.92}B_{3.28}$ and $Ni_{72.5}Cr_{4.5}Nb_{3.5}P_{16.5}B_3$ metallic glasses are presented in FIG. 8. The scans reveal that metallic glass alloy $Ni_{68.17}Cr_{8.65}Nb_{2.98}P_{16.92}B_{3.28}$, which demonstrated long $t_{cryst}$ in the temperature range of 525-675° C., also demonstrated a large ΔT of about 55° C. By contrast, metallic glass alloy $Ni_{72.5}Cr_{4.5}Nb_{3.5}P_{16.5}B_3$, which demonstrated short $t_{cryst}$ in the temperature range of 525-675° C., demonstrated a significantly smaller ΔT of about 42° C.

Figure 5:
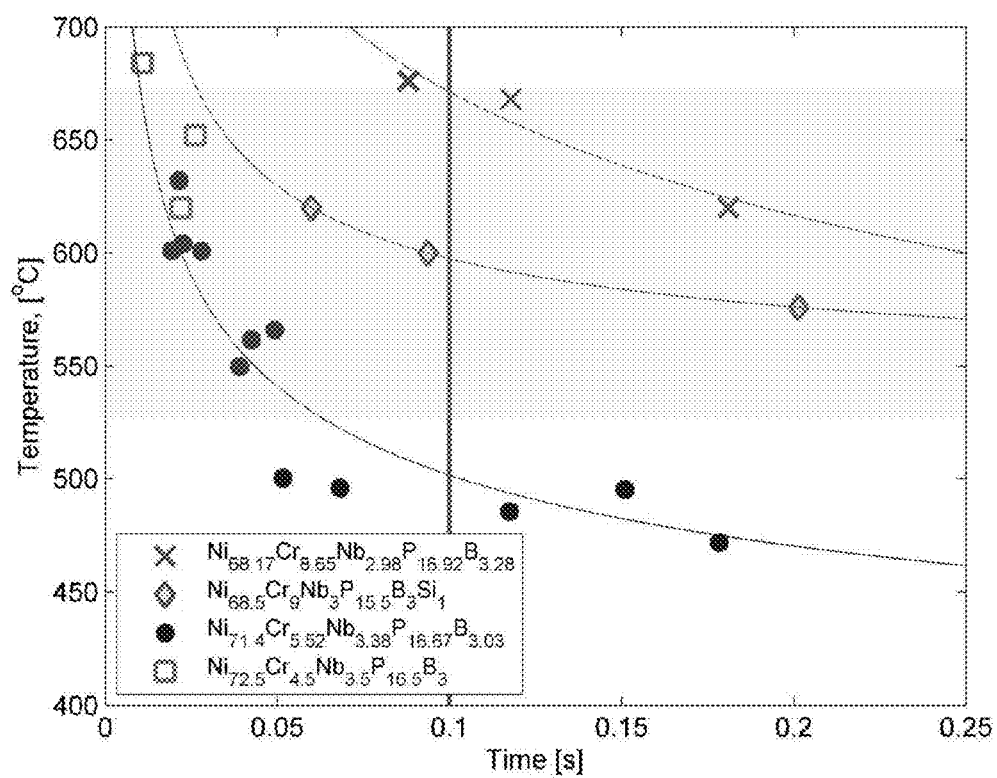
FIG. 5 provides a Time-Temperature-Transformation (TTT) plot for metallic glass alloys $Ni_{68.17}Cr_{8.65}Nb_{2.98}P_{16.92}B_{3.28}$, $Ni_{68.5}Cr_9Nb_3P_{15.5}B_3Si_1$, $Ni_{71.4}Cr_{5.52}Nb_{3.38}P_{16.67}B_{3.03}$, and $Ni_{72.5}Cr_{4.5}Nb_{3.5}P_{16.5}B_3$.
Figure 8:
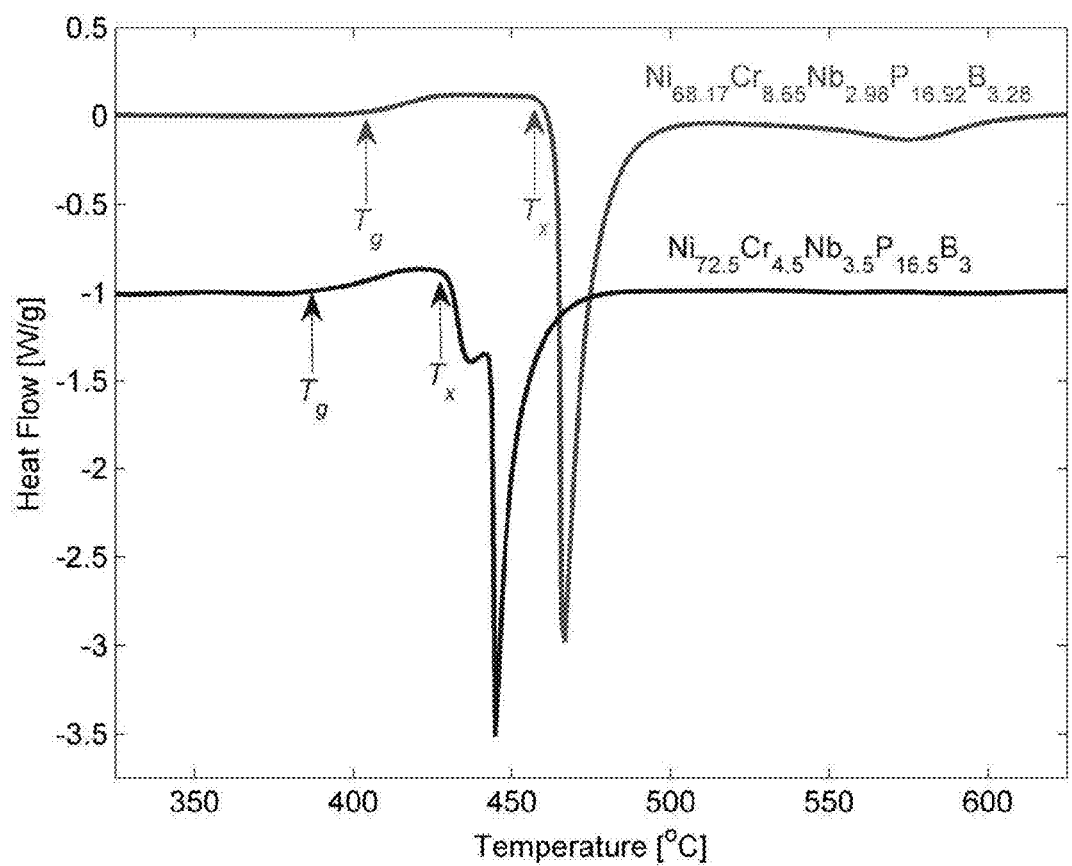
FIG. 8 provides differential calorimetry scans of metallic glass alloys $Ni_{72.5}Cr_{4.5}Nb_{3.5}P_{16.5}B_3$ and $Ni_{68.17}Cr_{8.65}Nb_{2.98}P_{16.92}B_{3.28}$.
Figure 9:
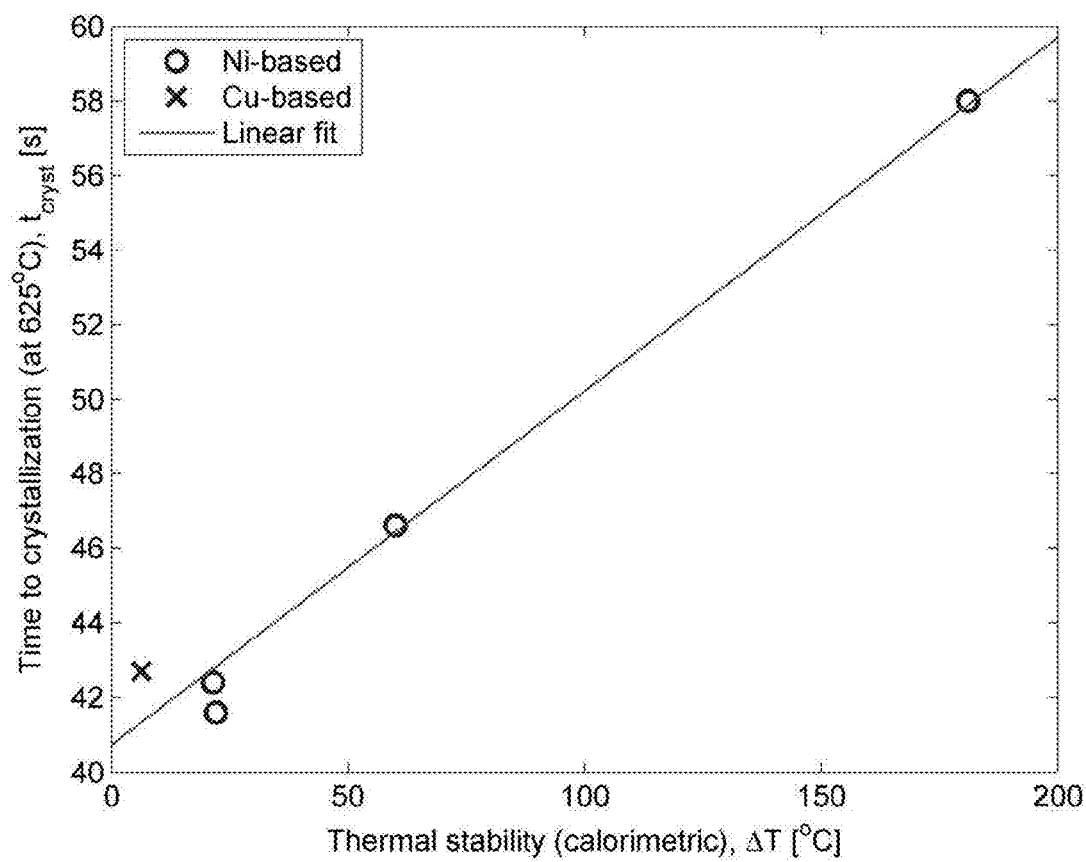
FIG. 9 provides a correlation between $t_{cryst}$ and $\Delta T(T_x-T_g)$ for metallic glass alloys $Ni_{68.17}Cr_{8.65}Nb_{2.98}P_{16.92}B_{3.28}$, $Ni_{68.5}Cr_9Nb_3P_{15.5}B_3Si_1$, $Ni_{71.4}Cr_{5.52}Nb_{3.38}P_{16.67}B_{3.03}$, $Ni_{72.5}Cr_{4.5}Nb_{3.5}P_{16.5}B_3$ and $Cu_{47}Ti_{33}Zr_{11}Ni_8Si_1$.

Differential scanning calorimetry was also performed for metallic glass alloys $Ni_{68.5}Cr_9Nb_3P_{15.5}B_3Si_1$, $Ni_{71.4}Cr_{5.52}Nb_{3.38}P_{16.67}B_{3.03}$, whose TTT curves are also presented in FIG. 5, and for metallic glass alloy $Cu_{47}Ti_{33}Zr_{11}Ni_8Si_1$, whose TTT curve is presented in FIG. 8. The data for $t_{cryst}$ and ΔT for each alloy are presented in Tables 1 and 2. A trend is revealed in Tables 1 and 2, where $t_{cryst}$ and ΔT appear to be correlated. In FIG. 9, $t_{cryst}$ at the temperature of 625° C. (which is within the viscosity range of $10^0$ to $10^4$ Pa-s for both Ni—based and Cu-based metallic glasses) is plotted against ΔT for metallic glass alloys $Ni_{68.17}Cr_{8.65}Nb_{2.98}P_{16.92}B_{3.28}$, $Ni_{68.5}Cr_9Nb_3P_{15.5}B_3Si_1$, $Ni_{71.4}Cr_{5.52}Nb_{3.38}P_{16.67}B_{3.03}$, $Ni_{72.5}Cr_{4.5}Nb_{3.5}P_{16.5}B_3$, and $Cu_{47}Ti_{33}Zr_{11}Ni_8Si_1$. FIG. 9 reveals a one-to-one correspondence between $t_{cryst}$ and ΔT when a linear regression of the data was performed (although some small variation from the regression can be seen). This correspondence suggests that the scanning calorimetry data may help identify the order from the least suitable to the most suitable alloy for RCDF processing of high aspect ratio articles. Specifically, the calorimetry data suggests that metallic glass alloys having ΔT>45° C., and in some embodiments ΔT>50° C., may have $t_{cryst}$>100 ms and thus would be capable of being shaped into high aspect ratio parts using RCDF according to the current disclosure. More Ni—based metallic glass alloys demonstrating ΔT>50° C. are listed in Table 3, whereas data for the respective glass forming ability (designated by the critical rod diameter $D_{cr}$) are also presented in Table 3. According to the present disclosure, some of these alloys may be shaped into high aspect ratio articles by RCDF.

The method of differential scanning calorimetry can be used to identify the most suitable alloys for RCDF within a specific alloy family. Calorimetry is a more standard and simpler method than generating actual RCDF heating curves. Differential scanning calorimetry is therefore a useful tool in screening compositions within a specific metallic glass family for RCDF processing of high aspect ratio parts.

TABLE 1

Crystallization times obtained by RCDF heating to various plateau temperatures for various Ni-based metallic glasses within the range of 525-675° C., and thermal stability data obtained by differential scanning calorimetry for the sample metallic glasses.

| Example | Composition | $t_{cryst}$ (ms) | $T_g$ (° C.) | $T_x$ (° C.) | ΔT (° C.) |
|---|---|---|---|---|---|
| 1 | $Ni_{68.17}Cr_{8.65}Nb_{2.98}P_{16.92}B_{3.28}$ | 88 | 402.9 | 460.9 | 58 |
|   |   | 118 |   |   |   |
|   |   | 181 |   |   |   |
| 2 | $Ni_{68.5}Cr_9Nb_3P_{15.5}B_3Si_1$ | 60 | 402 | 448.6 | 46.6 |
|   |   | 94 |   |   |   |
|   |   | 201 |   |   |   |
| 3 | $Ni_{71.4}Cr_{5.52}Nb_{3.38}P_{16.67}B_{3.03}$ | 20 | 393 | 435.4 | 42.4 |
|   |   | 22 |   |   |   |
|   |   | 23 |   |   |   |
|   |   | 28 |   |   |   |
|   |   | 39 |   |   |   |
|   |   | 43 |   |   |   |
|   |   | 49 |   |   |   |
| 4 | $Ni_{72.5}Cr_{4.5}Nb_{3.5}P_{16.5}B_3$ | 22 | 389 | 430.6 | 41.6 |
|   |   | 26 |   |   |   |

TABLE 2

Crystallization times obtained by RCDF heating to various plateau temperatures for metallic glass $Cu_{47}Ti_{34}Zr_{11}Ni_8$ within the range of 570-810° C., and thermal stability data obtained by differential scanning calorimetry for the sample metallic glass.

| Example | Composition | $t_{cryst}$ (ms) | $T_g$ (° C.) | $T_x$ (° C.) | ΔT (° C.) |
|---|---|---|---|---|---|
| 65 | $Cu_{47}Ti_{33}Zr_{11}Ni_8Si_1$ | 6 | 410.1 | 452.8 | 42.7 |
|   |   | 13 |   |   |   |
|   |   | 19 |   |   |   |
|   |   | 44 |   |   |   |
|   |   | 47 |   |   |   |
|   |   | 56 |   |   |   |

TABLE 3

Glass forming ability and thermal stability data for sample Ni-based alloys and metallic glasses.

| Example | Composition | $D_{cr}$ (mm) | $T_g$ (° C.) | $T_x$ (° C.) | T (° C.) |
|---|---|---|---|---|---|
| 1 | $Ni_{68.17}Cr_{8.65}Nb_{2.98}P_{16.92}B_{3.28}$ | 9 | 402.9 | 460.9 | 58 |
| 2 | $Ni_{68.5}Cr_9Nb_3P_{15.5}B_3Si_1$ | 7 | 402 | 448.6 | 46.6 |
| 5 | $Ni_{68.6}Cr_{8.7}Nb_3P_{16.5}B_{3.2}$ | 11 | 401.5 | 449.5 | 48 |
| 6 | $Ni_{68.5}Cr_9Nb_3P_{16}B_3Si_{0.5}$ | 9 | 398.2 | 443.8 | 45.6 |

TABLE 3-continued

Glass forming ability and thermal stability data for sample Ni-based alloys and metallic glasses.

| Example | Composition | $D_{cr}$ (mm) | $T_g$ (° C.) | $T_x$ (° C.) | T (° C.) |
|---|---|---|---|---|---|
| 7 | $Ni_{69}Cr_{8.5}Nb_3P_{16.5}B_3$ | 10 | 395.2 | 441.5 | 46.3 |
| 8 | $Ni_{69}Cr_{8.5}Nb_3P_{16}B_{3.5}$ | 8 | 396 | 442.7 | 46.7 |
| 9 | $Ni_{69}Cr_{8.5}Nb_3P_{15.75}B_{3.75}$ | 6 | 399.5 | 447.1 | 47.6 |
| 10 | $Ni_{68.5}Cr_{8.5}Nb_3P_{16}B_4$ | 5 | 398.5 | 454.6 | 56.1 |
| 11 | $Ni_{68.5}Cr_{8.5}Nb_3P_{15.5}B_{4.5}$ | 4 | 403.7 | 456.4 | 52.7 |
| 12 | $Ni_{68.5}Cr_{8.5}Nb_3P_{15}B_5$ | 4 | 401.4 | 453.8 | 52.4 |
| 13 | $Ni_{69}Cr_{10}Nb_{1.5}P_{16.5}B_3$ | 3 | 388.5 | 438.9 | 50.4 |
| 14 | $Ni_{69}Cr_{9.5}Nb_2P_{16.5}B_3$ | 4 | 389.7 | 443.4 | 54.9 |
| 15 | $Ni_{69}Cr_9Nb_{2.5}P_{16.5}B_3$ | 7 | 395.5 | 443.4 | 47.9 |
| 16 | $Ni_{67.5}Cr_{10}Nb_3P_{16.5}B_3$ | 8 | 398.6 | 443.9 | 45.3 |
| 17 | $Ni_{66.5}Cr_{11}Nb_3P_{16.5}B_3$ | 6 | 400 | 450.5 | 50.5 |
| 18 | $Ni_{65.5}Cr_{12}Nb_3P_{16.5}B_3$ | 6 | 401.4 | 451.8 | 50.4 |
| 19 | $Ni_{64.5}Cr_{13}Nb_3P_{16.5}B_3$ | 5 | 403.2 | 455.9 | 52.7 |
| 20 | $Ni_{63.5}Cr_{14}Nb_3P_{16.5}B_3$ | 5 | 406.4 | 458.3 | 51.9 |
| 21 | $Ni_{68.5}Cr_9Nb_3P_{15}B_3Si_{1.5}$ | 4 | 407 | 453.7 | 46.7 |
| 22 | $Ni_{68.17}Cr_{8.65}Nb_{2.98}P_{16.42}B_{3.28}Si_{0.5}$ | 8 | 404.6 | 462.4 | 57.8 |
| 23 | $Ni_{68.17}Cr_{8.65}Nb_{2.98}P_{15.92}B_{3.28}Si_1$ | 7 | 407.9 | 465.3 | 57.4 |
| 24 | $Ni_{67.75}Cr_{8.59}Nb_{2.96}P_{17.34}B_{3.36}$ | 6 | 406.9 | 468.3 | 61.4 |
| 25 | $Ni_{69}Cr_{10}Nb_{1.5}P_{18}B_{1.5}$ | 3 | 384.2 | 437.2 | 53 |
| 26 | $Ni_{69}Cr_{9.5}Nb_2P_{17.5}B_2$ | 4 | 386.8 | 437.8 | 51 |
| 27 | $Ni_{69}Cr_9Nb_{2.5}P_{17}B_{2.5}$ | 6 | 389.6 | 437.7 | 48.1 |
| 28 | $Ni_{69}Cr_8Nb_{3.5}P_{16}B_{3.5}$ | 9 | 398.7 | 447 | 48.3 |
| 29 | $Ni_{69}Cr_{7.5}Nb_4P_{15.5}B_4$ | 9 | 403.3 | 453 | 49.7 |
| 30 | $Ni_{69}Cr_7Nb_{4.5}P_{15}B_{4.5}$ | 7 | 409.6 | 454.6 | 45 |
| 31 | $Ni_{69}Cr_{8.75}Nb_{2.75}P_{16}B_{3.5}$ | 7 | 394.3 | 445.7 | 51.3 |
| 32 | $Ni_{69}Cr_9Nb_{2.5}P_{15.5}B_4$ | 6 | 390.1 | 444.3 | 54.2 |
| 33 | $Ni_{69}Cr_{9.25}Nb_{2.25}P_{15}B_{4.5}$ | 6 | 391.1 | 443.9 | 52.7 |
| 34 | $Ni_{69}Cr_{9.5}Nb_2P_{14.5}B_5$ | 7 | 389.8 | 441.2 | 51.4 |
| 35 | $Ni_{69}Cr_{9.75}Nb_{1.75}P_{14}B_{5.5}$ | 5 | 391.0 | 439.3 | 48.3 |
| 36 | $Ni_{69}Cr_{10}Nb_{1.5}P_{13.5}B_6$ | 4 | 391.5 | 438.7 | 47.2 |
| 37 | $Ni_{67.5}Co_{1.5}Cr_{8.5}Nb_3P_{16.5}B_3$ | 11 | 396 | 443.5 | 47.5 |
| 38 | $Ni_{66}Co_3Cr_{8.5}Nb_3P_{16.5}B_3$ | 10 | 397.3 | 446.3 | 49.0 |
| 39 | $Ni_{64}Co_5Cr_{8.5}Nb_3P_{16.5}B_3$ | 9 | 398.6 | 454.4 | 55.8 |
| 40 | $Ni_{59}Co_{10}Cr_{8.5}Nb_3P_{16.5}B_3$ | 8 | 401.2 | 458.6 | 57.4 |
| 41 | $Ni_{54}Co_{15}Cr_{8.5}Nb_3P_{16.5}B_3$ | 8 | 408.5 | 466.9 | 58.4 |
| 42 | $Ni_{49}Co_{20}Cr_{8.5}Nb_3P_{16.5}B_3$ | 7 | 411.2 | 464.5 | 53.2 |
| 43 | $Ni_{44}Co_{25}Cr_{8.5}Nb_3P_{16.5}B_3$ | 5 | 416.2 | 468.8 | 52.2 |
| 44 | $Ni_{61.4}Co_{10}Cr_{5.52}Nb_{3.38}P_{16.67}B_{3.03}$ | 8 | 400.6 | 453.9 | 53.3 |
| 45 | $Ni_{56.4}Co_{15}Cr_{5.52}Nb_{3.38}P_{16.67}B_{3.03}$ | 7 | 406.0 | 458.2 | 52.2 |
| 46 | $Ni_{51.4}Co_{20}Cr_{5.52}Nb_{3.38}P_{16.67}B_{3.03}$ | 5 | 408.3 | 460.7 | 52.4 |
| 47 | $Ni_{46.4}Co_{25}Cr_{5.52}Nb_{3.38}P_{16.67}B_{3.03}$ | 5 | 414.7 | 461.7 | 47.0 |
| 48 | $Ni_{67.1}Cr_{10}Nb_{3.4}P_{18}Si_{1.5}$ | 10 | 402.8 | 448.7 | 45.9 |
| 49 | $Ni_{66.1}Cr_{11}Nb_{3.4}P_{18}Si_{1.5}$ | 10 | 405.1 | 450.4 | 45.3 |
| 50 | $Ni_{64.1}Cr_{13}Nb_{3.4}P_{18}Si_{1.5}$ | 5 | 408.5 | 455.6 | 47.1 |
| 51 | $Ni_{62.1}Cr_{15}Nb_{3.4}P_{18}Si_{1.5}$ | 4 | 410.2 | 462.2 | 52.0 |
| 52 | $Ni_{68.5}Cr_{8.5}Mn_3P_{17}B_3$ | 4 | 384.6 | 434.1 | 49.5 |
| 53 | $Ni_{68.5}Cr_{7.5}Mn_3Mo_1P_{16.5}B_3$ | 5 | 379.4 | 432.4 | 53.0 |
| 54 | $Ni_{68.5}Cr_9Ta_3P_{16.5}B_3$ | 6 | 405.8 | 454.1 | 48.3 |
| 55 | $Ni_{68.5}Cr_9Ta_3P_{16.25}B_{3.25}$ | 7 | 407.8 | 455.6 | 47.8 |
| 56 | $Ni_{68.5}Cr_9Ta_3P_{16}B_{3.5}$ | 6 | 406.3 | 455.2 | 48.9 |
| 57 | $Ni_{68.5}Cr_9Ta_3P_{15.5}B_4$ | 5 | 406.3 | 460.0 | 53.7 |
| 58 | $Ni_{68.5}Cr_9Ta_3P_{15}B_{4.5}$ | 4 | 405.3 | 455.1 | 49.8 |
| 59 | $Ni_{69.5}Cr_8Ta_3P_{16.25}B_{3.25}$ | 6 | 404.3 | 450.6 | 46.3 |
| 60 | $Ni_{68.5}Cr_9Ta_3P_{16.25}B_{3.25}$ | 7 | 407.3 | 455.3 | 48.0 |
| 61 | $Ni_{67.5}Cr_{10}Ta_3P_{16.25}B_{3.25}$ | 6 | 407.3 | 455.8 | 48.5 |
| 62 | $Ni_{68.5}Cr_{10}Ta_2P_{16.25}B_{3.25}$ | 4 | 393.7 | 445.7 | 52.0 |
| 63 | $Ni_{68.5}Cr_{9.5}Ta_{2.5}P_{16.25}B_{3.25}$ | 5 | 401.1 | 450.1 | 49.0 |
| 64 | $Ni_{68.5}Cr_{8.5}Ta_{3.5}P_{16.25}B_{3.25}$ | 4 | 409.2 | 455.1 | 45.9 |

Methods

Experimental Procedure for Generating the RCDF Heating Curves

Ni—based metallic glass feedstock rods with a nominal diameter of 5 mm and Cu-based metallic glass feedstock strips 1 mm in thickness and 5 mm in width were verified to be amorphous by X-ray diffraction. The Ni—based metallic glass feedstock rods with diameters ranging between 4.83 to 4.91 mm were clamped on each end between two copper plates with a cylindrical hole slightly smaller than the diameter of the samples with exposed length between 7.28 mm and 36.96 mm. The exposed length was sheathed with a fused silica tube with nominal inner diameter of 5 mm and nominal outer diameter of 7 mm. Copper plates were clamped in a vise and attached to the leads of the capacitive discharge circuit. The fused silica sheath was supported so that when the sample heated and sagged under gravity, the sheath and sample would not shift. The Cu-based metallic glass feedstock strips were clamped on each end between two copper plates with exposed length of about 10 to 20 mm. A high-speed infrared pyrometer with a response time of 6 is and an Indium-Gallium-Arsenide sensor with a spectral range of 1.58-2.2 µm were used to measure the temperature at the midpoint of the exposed sample (for the rods, through the fused silica sleeve). A Rogowski coil current sensor and voltage probe were used to measure current and voltage, respectively, of the capacitive discharge pulse. Data from these sources were collected with an oscilloscope. Current and voltage data were used to verify that there were no anomalies in the shape of the current pulse. The temperature data shows a rapid heating during the current pulse, then a period of relatively constant temperature, then another period of increasing temperature due to the exothermic crystallization transition, and finally another period of relatively constant temperature before the data acquisition terminates. The time to crystallization $t_{cryst}$ was measured from the initiation of the current pulse to the onset of the temperature increase caused by crystallization.

Experimental Procedure for Molding High Aspect Ratio Parts Using RCDF

Metallic glass feedstock rods with a nominal diameter of 4 mm were verified to be amorphous by X-ray diffraction. The two ends of each rod were polished substantially parallel to each other and perpendicular to the axis of the rod, and subsequently ground to 180 grit surface finish. The rods were then confined within a fused silica sleeve with a copper electrode/plunger on each end. The fused silica was prepared so that two openings were ground into the sleeve and aligned with the gates of a stainless steel mold with a toroidal cavity having high aspect ratio features. Some of the cavity features had aspect ratio of about 10 and thickness of about 1 mm. This assembly of mold, sleeve, feedstock and electrodes was placed under compression along the axis of the feedstock and electrodes, and the electrodes were connected to the leads of the capacitor discharge circuit. The capacitors were discharged, and the material heated and flowed through the gates and into the toroidal mold cavity under the applied pressure. The injection molding of $Ni_{68.17}Cr_{8.65}Nb_{2.98}P_{16.92}B_{3.28}$ was performed using a 23 mm long rod of feedstock. The successfully shaped high aspect ratio article is shown in FIG. 3B. The current pulse was set to deliver 3700 J/cm³ to the sample, and was deformed under a pressure of about 50 MPa. The injection molding of $Ni_{71.4}Cr_{5.52}Nb_{3.38}P_{16.67}B_{3.03}$ was performed using a 16 mm long rod of feedstock. The unsuccessfully shaped article is shown in FIG. 3A. The current pulse was set to deliver 4300 J/cm³ to the sample, and was deformed under a pressure of about 40 MPa. The energy in both experiments was carefully selected to result in heating to a temperature within a selected range of 525-675° C.

Experimental Procedure for Measuring Viscosity

The equilibrium (Newtonian) viscosity for $Ni_{68.17}Cr_{8.65}Nb_{2.98}P_{16.42}B_{3.28}Si_{0.5}$ metallic glass alloy was measured by performing three point beam bending of metallic glass rods 2 mm in diameter and 10 mm in length using a thermo-mechanical analyzer (PerkinElmer TMA 7), as described by Hagy (H. E. Hagy, "Experimental Evaluation of Beam Bending Method of Determining Glass Viscosities in the Range $10^8$ to $10^{15}$ Poise", J. Am. Ceram. Soc. 46, 93 (1963), the reference of which is incorporated herein in its entirety). Specifically, the isothermal viscosity at a given temperature is determined by the following equation:

$$\eta = -\frac{gL^3}{144I_c v}\left(M + \frac{5\rho A L}{8}\right) \qquad \text{EQ. 3}$$

where $\eta$ is the apparent viscosity (Pa-s), g the gravitational constant (m/s²), L the support span length (m), $I_c$ the cross sectional moment of inertia (m⁴), v the midpoint deflection velocity (m/s), M the applied load (kg), $\rho$ the density (kg/m³), and A is the cross sectional area (m²). Loads ranging from 20 to 1000 mN were applied.

Data for the equilibrium (Newtonian) viscosity for $Ni_{68.17}Cr_{8.65}Nb_{2.98}P_{16.42}B_{3.28}Si_{0.5}$ metallic glass alloy $Cu_{47}Ti_{34}Zr_{11}Ni_8$ were taken from Glade and Johnson (S. C. Glade and W. L. Johnson, "Viscous Flow of the $Cu_{47}Ti_{34}Zr_{11}Ni_8$ Glass-Forming Alloy", J. Appl. Phys. 87, 7249 (2000), the reference of which is incorporated herein in its entirety).

Analytical Procedure for Fitting the Viscosity Data

To describe the temperature dependence of viscosity $\eta(T)$, the cooperative shear model of Johnson et al. (W. L. Johnson, M. D. Demetriou, J. S. Harmon, M. L. Lind, and K. Samwer, "Rheology and Ultrasonic Properties of Metallic Glass Forming Liquids: a Potential Energy Landscape Perspective", MRS Bulletin, 32, 644 (2007), the reference of which is incorporated herein in its entirety) is employed:

$$\frac{\eta(T)}{\eta_\infty} = \exp\left\{\frac{W_g}{kT}\exp\left[2n\left(1 - \frac{T}{T_{go}}\right)\right]\right\} \qquad \text{EQ. 4}$$

where $\eta_\infty$ the high-temperature limit of viscosity, $W_g$ is the activation energy barrier at the glass transition, approximated by $W_g \approx kT_{go} \log(\eta_g/\eta_\infty)$ (where $\eta_g=1\times10^{12}$ Pa-s, n is the effective fragility parameter, k the Boltzmann constant, T is temperature (in units of Kelvin), and $T_{go}$ the glass transition temperature associated with a the viscosity value of $10^{12}$ Pa-s (in units of Kelvin). The fitting parameters $Ni_{68.17}Cr_{8.65}Nb_{2.98}P_{16.42}B_{3.28}Si_{a5}$ and $Cu_{47}Ti_{34}Zr_{11}Ni_8$ metallic glass alloys are given in Table 4.

TABLE 4

Model parameters for fitting the viscosity data for $Ni_{68.17}Cr_{8.65}Nb_{2.98}P_{16.42}B_{3.28}Si_{0.5}$ and $Cu_{47}Ti_{34}Zr_{11}Ni_8$ metallic glass alloys.

| Composition | $T_{go}$ (K) | n | $\eta_\infty$ (Pa-s) |
|---|---|---|---|
| $Ni_{68.17}Cr_{8.65}Nb_{2.98}P_{16.42}B_{3.28}Si_{0.5}$ | 673.4 | 1.553 | 0.001 |
| $Cu_{47}Ti_{34}Zr_{11}Ni_8$ | 657.8 | 0.9431 | 0.002 |

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

We claim:

1. A method of forming an article having an aspect ratio of at least 10 from a metallic glass alloy, the method comprising:
   selecting a metallic glass alloy having a crystallization time $t_{cryst}$ at least 100 ms at a temperature above the glass transition of the metallic glass where the viscosity of the metallic glass alloy is in the range of $10^0$ to $10^4$ Pa-s;
   applying a quantum of electrical energy to a feedstock comprising the metallic glass alloy and having a uniform cross section using a capacitive discharge forming system to heat the feedstock to a temperature above the glass transition of the metallic glass;

shaping the heated feedstock into an article having an aspect ratio of at least 10, wherein the time to shape $t_s$ is less than $t_{cryst}$, and $t_s$ is greater than 100 ms at a temperature where the viscosity of the metallic glass alloy is in the range of $10^0$ to $10^4$ Pa-s; and cooling the shaped article to a temperature below the glass transition temperature of the metallic glass alloy to avoid crystallization of the metallic glass, wherein the time to cool said article $t_c$ is less than $t_{cryst}$.

2. The method of claim 1, where the article has thickness of 2 mm or less.

3. The method of claim 1, wherein the article thickness is from 0.5 mm to 2 mm.

4. The method of claim 1, wherein the viscosity is from $10^1$ to $10^3$ Pa-s.

5. The method of claim 1, wherein the viscosity is from $10^2$ to $10^4$ Pa-s.

6. The method of claim 1, wherein said shaping is subsequent to said applying.

7. The method of claim 1, wherein the shaping is selected from molding, forging, and casting.

8. The method of claim 1, wherein the metallic glass alloy is Zr-based, Ti-based, Ta-based, Y-based, Hf-based, Ni-based, Pd-based, Pt-based, Fe-based, Ni-based, Co-based, Cu-based, Au-based, Al-based, La-based, Ce-based, Pr-based, Nd-based, Gd-based, Mg-based, or Ca-based metallic glass alloy.

9. The method of claim 1, wherein the metallic glass alloy comprises the formula $X_{100-a-b}Y_aZ_b$, wherein
X is Ni, Fe, Co or a combination thereof,
Y is Cr, Mo, Mn, Nb, Ta or a combination thereof,
Z is P, B, C, Si, Ge or a combination thereof,
a is between 5 and 15 atomic %, and
b is between 15 and 25 atomic %.

10. The method of claim 1, wherein the metallic glass alloy is selected from a Ni—Cr—Nb—P—B, Ni—Cr—Ta—P—B, Ni—Cr—Mn—P—B, Ni—Mo—Nb—Mn—P—B, Ni—Mn—Nb—P—B, Ni—Cr—Mo—Si—B—P, and Ni—Fe—Si—B—P metallic glass alloy.

11. The method of claim 1, wherein the metallic glass alloy comprises the formula $Ni_{100-a-b-c-d}X_aY_bP_cZ_d$, wherein
X is Cr, Mo, Mn or combinations thereof
Y is Nb, Ta, Mn or combinations thereof
Z is B, Si or combinations thereof
a is between 3 and 15 atomic %
b is between 1 and 6 atomic %
c is between 12 and 20 atomic %
d is between 0.5 and 6 atomic %.

12. The method of claim 1, wherein the metallic glass alloy crystallizes at a temperature $T_x$ that is at least 45° C. higher than its glass transition temperature $T_g$ when heated by a constant heating rate of 0.67° C./s.

13. The method of claim 1, wherein the viscosity is from $10^1$ to $10^3$ Pa-s.

14. The method of claim 1, wherein the viscosity is from $10^2$ to $10^4$ Pa-s.

15. A metallic glass article produced by the process according to claim 1.

* * * * *

UNITED STATES PATENT AND TRADEMARK OFFICE
CERTIFICATE OF CORRECTION

PATENT NO. : 9,845,523 B2  
APPLICATION NO. : 14/216565  
DATED : December 19, 2017  
INVENTOR(S) : Joseph P. Schramm et al.

Page 1 of 1

It is certified that error appears in the above-identified patent and that said Letters Patent is hereby corrected as shown below:

(Claim 1) Column 16, Line 59, add "of" between "$t_{cryst}$" and "at least"

Signed and Sealed this  
Third Day of April, 2018

Andrei Iancu  
*Director of the United States Patent and Trademark Office*